US012799054B1

(12) United States Patent
Borras et al.

(10) Patent No.: US 12,799,054 B1
(45) Date of Patent: Nov. 17, 2026

(54) FOAM SEPARATION OF PERFLUORO- AND POLYFLUORO-ALKYL COMPOUNDS UNDER ACIDIC CONDITIONS

(71) Applicant: NuQuatic, LLC, St. Paul, MN (US)

(72) Inventors: Carlos Borras, Ruskin, FL (US); Donald A. Luke, Valrico, FL (US); Kyle Broaddrick, Brookfield, WI (US)

(73) Assignee: NuQuatic, LLC, St. Paul, MN (US)

( * ) Notice: Subject to any disclaimer, the term of this patent is extended or adjusted under 35 U.S.C. 154(b) by 0 days.

(21) Appl. No.: 19/444,084

(22) Filed: Jan. 8, 2026

Related U.S. Application Data

(63) Continuation-in-part of application No. PCT/US2025/036696, filed on Jul. 7, 2025.

(60) Provisional application No. 63/668,476, filed on Jul. 8, 2024.

(51) Int. Cl.
*C07C 17/42* (2006.01)
*C07C 17/389* (2006.01)

(52) U.S. Cl.
CPC ............ *C07C 17/42* (2013.01); *C07C 17/389* (2013.01)

(58) Field of Classification Search
CPC .............................. C07C 17/42; C07C 17/389
See application file for complete search history.

(56) References Cited

U.S. PATENT DOCUMENTS

| | | | |
|---|---|---|---|
| 10,752,521 | B2 | 8/2020 | Nelson |
| 11,358,103 | B2 | 6/2022 | Phillips et al. |
| 11,975,369 | B2 | 5/2024 | Phillips et al. |
| 12,139,420 | B2 | 11/2024 | Phillips et al. |
| 2014/0001102 | A1 | 1/2014 | Blendinger et al. |
| 2014/0110311 | A1 | 4/2014 | Le Roux Cillier et al. |
| 2023/0127819 | A1 | 4/2023 | Townsend et al. |
| 2025/0178927 | A1 | 6/2025 | Phillips et al. |

OTHER PUBLICATIONS

En We, Angel Chyi, "A review of foam fractionation for the removal of per- and polyfluoroalkyl substances PFAS from aqueous matrices", Journal Of Hazardous Materials 465 133182, 2024, 17 pgs.
"International Application Serial No. PCT/US2025/036696, International Search Report mailed Sep. 18, 2025", 3 pgs.
"International Application Serial No. PCT/US2025/036696, Written Opinion mailed Sep. 18, 2025", 9 pgs.
Lee, Yu-Chi, et al., "Recovery of perfluorooctane sulfonate (PFOS) and perfluorooctanoate (PFOA) from dilute water solution by foam flotation", Separation and Purification Technology vol. 173, [Online] Retrieved from the internet: <http://dx.doi.Org/10.1016/j.seppur.2016.09.012>, (Sep. 21, 2016), 280-285.

(Continued)

*Primary Examiner* — Jafar F Parsa
(74) *Attorney, Agent, or Firm* — Schwegman Lundberg & Woessner, P.A.

(57) ABSTRACT

A method of concentrating a fluoroalkyl compound includes bubbling a gas into an aqueous solution including the fluoroalkyl compound and having a pH of 0 to 5.5 to form a foam that includes the fluoroalkyl compound. The method also includes removing the foam from the aqueous solution to form a concentrate including the fluoroalkyl compound and to form a clarified aqueous solution.

19 Claims, 9 Drawing Sheets

(56) References Cited

OTHER PUBLICATIONS

Rahman, Nazeri Abdul, et al., “Kinetic Study & Statistical Modelling of Sarawak Peat Water Electrocoagulation System using Copper and Aluminium Electrodes”, Journal of Applied Science & Process Engineering vol. 7, No. 1, pp. 439-456, (Apr. 30, 2020), 18 pgs.
Smith, et al., “Electrochemical Oxidation for Treatment of PFAS in Contaminated Water and Fractionated Foam—A Pilot-Scale Study”, ACS ES&T Water vol. 3 (4), [Online] Retrieved from the internet: <DOI:10.1021/acsestwater.2c0066>, (Mar. 15, 2023), 1201-1209.
Stevenson, Paul, et al., “Foam Fractionation”, Principles and Process Design, 202 pgs.

FOAM SEPARATION OF PERFLUORO- AND POLYFLUORO-ALKYL COMPOUNDS UNDER ACIDIC CONDITIONS

CROSS-REFERENCE TO RELATED APPLICATION

This application is a continuation-in-part of and claims the benefit of priority under 35 U.S.C. § 120 to PCT Application PCT/US2025/036696 filed Jul. 7, 2025, which claims the benefit under 35 U.S.C. § 119(e) of U.S. Provisional Patent Application Ser. No. 63/668,476 filed Jul. 8, 2024, the disclosures of which are incorporated herein in their entirety by reference.

BACKGROUND

Perfluoroalkyl or polyfluoroalkyl substances (PFASs) embody a range of polyfluorinated alkyl substances including but not limited to carboxylic acids, alkyl sulfonates, alkyl sulfonamide compounds, and fluorotelemer compounds of differing carbon chain lengths and precursors thereof. PFASs have found use in a wide variety of applications including as a specialized fire-fighting product, or for impregnation or coating of textiles, leather and carpet, or for carpet cleaning compounds, as well as in aviation hydraulic fluids, metal plating, agricultural (e.g., insect traps for certain types of ants), photo-imaging, electronics manufacture, and non-stick cookware applications.

Higher order PFASs degrade to specific end-point PFAS chemicals including but not limited to perfluorooctane sulfonate (PFOS), perfluorooctanoic acid (PFOA) and perfluorohexane sulfonate (PFHxS). These compounds of concern are resistant to biotic or abiotic degradation and thus are persistent in the environment. They are recalcitrant, bioaccumulative, and known to contaminate soils, groundwaters, and drinking water supplies.

PFASs are known to have contaminated groundwater, including drinking water supplies. PFOS, PFHxS, and PFOA have published human health and environmental regulatory criteria in most developed world jurisdictions. Additional PFASs are expected to be identified as contaminants of concern as new research toxicology data indicates potential risk associations.

Conventional techniques for treatment of water, such as to remove phosphorus, perfluoroalkyl or polyfluoroalkyl substances (PFASs), emulsions, and the like, suffer from problems of inefficiency, ineffectiveness, lack of versatility, high expense, and complex implementation.

SUMMARY OF THE INVENTION

Various aspects of the present invention provide a method of concentrating a fluoroalkyl compound. The method includes bubbling a gas into an aqueous solution including the fluoroalkyl compound and having a pH of 0 to 5.5 to form a foam including the fluoroalkyl compound. The method also includes removing the foam from the aqueous solution to form a concentrate including the fluoroalkyl compound and to form a clarified aqueous solution.

Various aspects of the present invention provide a method of concentrating a fluoroalkyl compound. The method includes bubbling a gas into an aqueous solution including the fluoroalkyl compound, an additive, and having a pH of 0 to 5.5 to form a foam including the fluoroalkyl compound. The additive includes a metal component including a metal. The method also includes removing the foam from the aqueous solution to form a concentrate including the fluoroalkyl compound and to form a clarified aqueous solution.

Various aspects of the present invention provide a method of concentrating a fluoroalkyl compound. The method includes bubbling a gas into an aqueous solution to form a foam including the fluoroalkyl compound. The aqueous solution has a pH of 0 to 5.5 and includes the fluoroalkyl compound at a concentration of 0.1 ppt to 100,000 ppm and an additive including a metal component that includes a metal. The method includes removing the foam from the aqueous solution to form a concentrate including the fluoroalkyl compound and to form a clarified aqueous solution including the metal of the metal component of the additive. A ratio of a concentration of the fluoroalkyl compound in the aqueous solution to a concentration of the fluoroalkyl compound in the concentrate is 1:2 to 1:2,000,000. The method also includes reusing the metal from the clarified aqueous solution or an extract thereof, the reusing including adding the metal to the aqueous solution of a subsequent iteration of the method or to feed water from which the fluoroalkyl compound in the aqueous solution is concentrated in the subsequent iteration of the method.

Various aspects of the present invention provide a method of concentrating a fluoroalkyl compound. The method includes bubbling a gas into an aqueous solution including the fluoroalkyl compound at a concentration of 0.1 ppt to 100,000 ppm and an additive including a metal component that includes aluminum to form a foam including the fluoroalkyl compound, wherein the aqueous solution has a pH of 0 to 5.5. The method includes removing the foam from the aqueous solution, wherein the aqueous solution having had the foam removed therefrom is a second aqueous solution. The method includes bubbling the gas into the second aqueous solution to form a second foam and removing the second foam from the second aqueous solution, and combining the foam removed from the aqueous solution and the second foam to form a concentrate including the fluoroalkyl compound, and wherein the second aqueous solution having the second foam removed therefrom is a clarified aqueous solution including the aluminum of the metal component. The method includes reusing the aluminum in the clarified aqueous solution or an extract thereof, the reusing including adding the aluminum to the aqueous solution. The method includes bubbling the gas into the concentrate to form a secondary foam including the fluoroalkyl compound the removing the secondary foam from the concentrate to form a secondary concentrate including the fluoroalkyl compound and to form a secondary clarified aqueous solution, wherein during the formation of the secondary foam the concentrate has a pH of 0 to less than 4, wherein a ratio of a concentration of the fluoroalkyl compound in the aqueous solution to a concentration of the fluoroalkyl compound in the secondary concentrate is 1:2 to 1:2,000,000. The method also includes recycling the secondary clarified aqueous solution back to the aqueous solution.

Various aspects of the method of the present invention provide certain advantages over other methods of treating water. For example, in various aspects, the method of the present invention can remove fluoroalkyl compounds from water more efficiently and/or with greater effectiveness as compared to other methods. In various aspects, the method of the present invention can produce concentrate containing fluoroalkyl compound having a higher concentration than that produced by other methods, which can provide a more efficient destruction of the fluoroalkyl compound with treatment of a smaller volume of liquid or solid than other methods. In various aspects, foam separation of various fluoroalkyl compounds can be more effective under the presently described acidic conditions as compared to foam separation of the compounds under higher pH conditions (e.g., pH above 5.5, or neutral pH, or basic pH). In various aspects, under the presently described acidic conditions, various fluoroalkyl compounds exist in a protonated form that is more amenable to foam separation than the deprotonated form existing under higher pH conditions.

Various aspects of the present method can include adding an additive including a metal component including a metal (e.g., an ion of a metal, a solid or dissolved compound of the metal, an elemental form of the metal, or a combination thereof) to the aqueous solution including the fluoroalkyl compound or to feed water from which the fluoroalkyl compound in the aqueous solution is concentrated, and recycling the metal of the metal component as the additive of a subsequent iteration of the method. In various aspects, the additive is used to concentrate the fluoroalkyl compound to form the aqueous solution. Addition and/or recycling the metal component can enhance of the efficiency of removal of the fluoroalkyl compound from the feed water and/or aqueous solution, and can overall decrease costs and increase efficiency of the process.

Various aspects of the present method can include purging acidification contaminants prior to recycling the metal of the metal component back to the contaminated water. By removing acidification contaminants, the build-up of the acidification contaminants in the recycle loop of the system can be decreased or entirely avoided. By removing acidification contaminants, the method can avoid introducing various chemical species into the water being treated is concentrations greater than permitted by environmental regulations.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
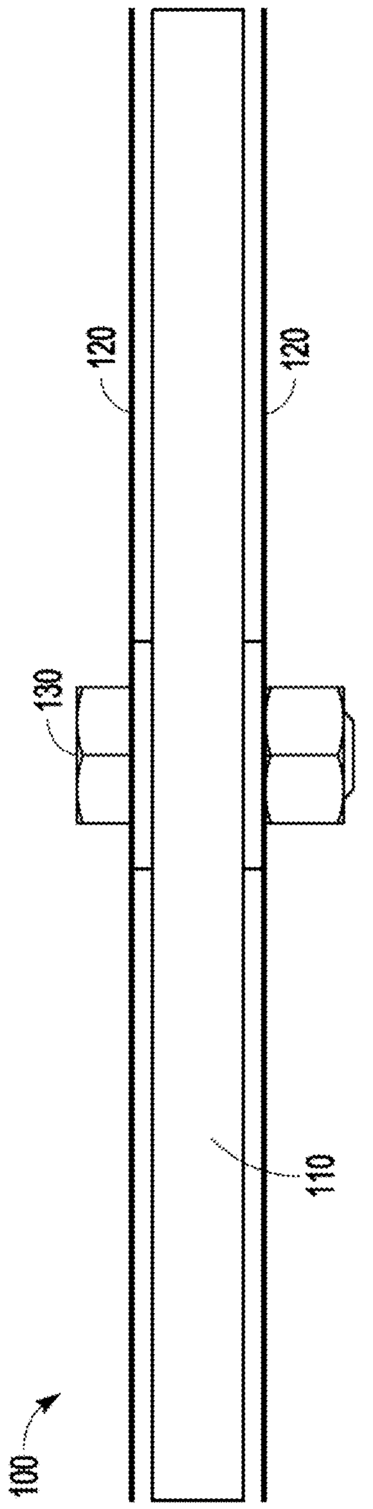
FIG. 1 illustrates a side-view of a galvanic cell including an anode that is a plate or strip, two cathodes that are screens, and a conductive connective maintaining a gap therebetween, in accordance with various aspects.

Reference will now be made in detail to certain aspects of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in a specific order as recited herein. Alternatively, in any aspect(s) disclosed herein, specific acts may be carried out in any order without departing from the principles of the invention, except when a temporal or operational sequence is explicitly recited. Furthermore, specified acts can be carried out concurrently unless explicit claim language recites that they be carried out separately or the plain meaning of the claims would require it. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

As used herein, the term "polymer" refers to a molecule having at least one repeating unit and can include copolymers.

Method of Concentrating a Fluoroalkyl Compound.

Various aspects of the present invention provide a method of concentrating a fluoroalkyl compound. The method can include bubbling a gas into an aqueous solution including the fluoroalkyl compound and having a pH of 0 to 5.5 to form a foam including the fluoroalkyl compound. The method can include removing the foam from the aqueous solution to form a concentrate including the fluoroalkyl compound and to form a clarified aqueous solution.

The fluoroalkyl compound can be any suitable fluoroalkyl compound. The fluoroalkyl compound can have a perfluoroalkyl or polyfluoroalkyl substance (PFAS), perfluoroalkyl substance, a polyfluoroalkyl substance, a perfluoroalkyl acid (PFAA), or a combination thereof. The fluoroalkyl compound can be perfluorooctanesulfonic acid (PFOA), perfluorooctyl sulfonate (PFOS), perfluorohexanesulfonic acid (PFHxS), perfluorononanoic acid (PFNA), perfluorobutanesulfonic acid (PFBS), 2-(N-methyl-perfluorooctane sulfonamido) acetic acid, perfluoroheptanoic acid (PFHpA), n-perfluorooctane sulfonic acid, perfluoromethylheptane sulfonic acid, n-perfluorooctanoic acid, a branched perfluorooctanoic acid, perfluorodecanoic acid, perfluoroundecanoic acid, perfluorododecanoic acid, hexafluoropropylene oxide-dimer acid (HFPO-DA), trifluoroacetic acid (TFA), trifluoromethanesulfonic acid (TFMS), or a combination thereof. The fluoroalkyl compound can be a short chain fluoroalkyl compound having 7 or less carbon atoms. The fluoroalkyl compound can be a medium or long chain fluoroalkyl compound having 8 or more carbon atoms. The method can be used to concentrate a single fluoroalkyl compound or a mixture of fluoroalkyl compounds.

The method of concentrating the fluoroalkyl compound can be characterized as foam fractionation, froth flotation, ion flotation, adsorptive bubble separation, bubble fractionation, multiphase separation, or a combination thereof. The fluoroalkyl compound can be an amphipathic molecule having both a hydrophilic region and a hydrophobic region. In various aspects, the fluoroalkyl compound can associate with a metal component such as aluminum hydroxide to form a hydrophobic particle that preferentially partitions to a gas-liquid interface. Under acidic conditions, complexes of the fluoroalkyl compound with ionic aluminum can form molecules having increased amphipathicity relative to the fluoroalkyl compound alone. The method can include ion flotation, wherein metal ions such as aluminum ions are captured and recovered in the foam phase along with the fluoroalkyl compound.

The method can include manipulating a surface tension or a surface energy of the aqueous solution to promote partitioning of the fluoroalkyl compound to the gas-liquid interface. Reagents can be added to the aqueous solution to modify the gas-liquid interface or particle surface properties. The metal component can function as a frother, a collector, an activator, a depressant, or a combination thereof, depending on the solution conditions. A frother can include a surface-active molecule that adsorbs at the gas-liquid interface to reduce surface energy and stabilize foam. A collector can include a substance that adsorbs to a surface to enhance hydrophobicity and promote attachment to gas bubbles. An activator can include a substance that promotes selective adsorption of a target species to a bubble surface. A depressant can include a substance that inhibits adsorption of a non-target species to a bubble surface.

The gas bubbled into the aqueous solution can be any suitable gas that forms the foam. The gas can include air, nitrogen, oxygen, ozone, argon, hydrogen, helium, or a combination thereof. In various aspects, the gas can include air. The gas can be a compressed or pressurized gas. The bubbling can include flowing the gas into an aeration apparatus that is submerged in the aqueous solution. The aeration apparatus can include a gas sparger, a perforated pipe, a sparging rod, a serrated cone, a diffuser ring, a stone diffuser, or a combination thereof. The aeration apparatus can include a stone diffuser, such as a porous stone that produces small bubbles when a gas is pumped therethrough. The aeration apparatus or bubble generating device can include a porous sparger, a sintered glass sparger, a sintered metal sparger, a metal frit, a perforated plate sparger, a perforated pipe, a single-orifice sparger, a multi-orifice sparger, a dynamic sparger with liquid cross-flow, a venturi, a needle wheel pump, a membrane diffuser, an ejector, a plunging liquid jet, or a combination thereof. The sparger can have a pore size of 10 microns to 1000 microns, or 10 microns to 200 microns, or less than or equal to 1000 microns and greater than or equal to 10 microns and less than, equal to, or greater than 16 microns, 20, 25, 40, 50, 60, 70, 80, 90, 100, 135, 150, 200, 250, 500, or 750 microns. Dynamic spargers utilizing liquid cross-flow can produce smaller bubble sizes than static spargers. The selection of the bubble generating device can be based on a desired bubble size distribution, a gas flow rate, a pressure drop, power consumption, or a combination thereof. The bubbling of the gas into the aqueous solution can form nanobubbles, microbubbles, or a combination thereof, wherein the bubbles include the gas. The bubbles can have a diameter (e.g., a diameter of one or more individual bubbles, or an number average diameter of the bubbles) of 1 nm to 10 mm, or 1 nm to 1000 nm, or 1000 nm to 1 mm, or 1 mm to 10 mm, or less than or equal to 10 mm and greater than or equal to 1 nm and less than, equal to, or greater than 2 nm, 5, 10, 20, 40, 60, 80, 100, 150, 200, 250, 300, 400, 500, 600, 700, 800, 900 nm, 1 micron, 2, 5, 10, 20, 40, 60, 80, 100, 150, 200, 250, 300, 400, 500, 600, 700, 800, 900 microns, 1 mm, 2, 3, 4, 5, 6, 7, 8, or 9 mm.

The method can include performing the bubbling of the gas into the aqueous solution in any suitable apparatus. In various aspects, the apparatus can include a column or tank. The apparatus can include a multi-stage column. The apparatus can include a multi-stage column with bubble cap trays. The apparatus in which the gas is bubbled into the aqueous solution to form the foam can include a column having a cylindrical geometry, a tapered geometry, a conical geometry, or a combination thereof. The apparatus can include a tapered section that narrows in a direction of foam rise to increase foam velocity and promote drainage. The apparatus can include multiple foam risers extending from a liquid pool zone to a foam collection zone. The apparatus can include mechanical means for enhancing foam stability or promoting foam collapse, such as rotating paddles, impellers, vibrating elements, ultrasonic transducers, spray nozzles, or humidity manipulation. The foam can be collected in any suitable way, such as using an inverted-U overflow pipe, a launder, a donut launder, a ring launder, an annular trough, a narrowed pipe overflow, a side port, a foam collection chamber, a weir, a skimmer, a vacuum extraction device, an overflow lip, or a combination thereof. The foam collection method can include combinations of flow contraction, expansion, and bending. Drainage enhancement can be achieved using internal components such as parallel inclined channels or foam riser plates that provide routes for interstitial liquid to drain back to the liquid pool.

The bubbling can be performed at a superficial gas velocity of 1 mm/s to 30 mm/s, or 1 mm/s to 12 mm/s, or 1 mm/s to 2 mm/s, or less than or equal to 30 mm/s and greater than or equal to 1 mm/s, and less than, equal to, or greater than 2 mm/s, 3, 4, 5, 6, 7, 8, 9, 10, 11, 12, 15, 20, or 25 mm/s. The gas flow rate can be 0.1 L/min to 1000 L/min, or 1 L/min to 100 L/min, or less than or equal to 1000 L/min and greater than or equal to 0.1 L/min, and less than, equal to, or greater than 0.5 L/min, 1, 2, 5, 10, 20, 50, 100, 200, 500, or 750 L/min. The gas flow rate can be selected based on a cross-sectional area of the apparatus, a volume of the aqueous solution, a concentration of the fluoroalkyl compound, a required throughput, or a combination thereof. The bubbles can have a Sauter mean radius of 0.1 mm to 5.5 mm, or 0.18 mm to 1 mm, or 0.5 mm to 1 mm, or less than or equal to 5.5 mm and greater than or equal to 0.1 mm, and less than, equal to, or greater than 0.15 mm, 0.18, 0.2, 0.3, 0.4, 0.5, 0.6, 0.7, 0.8, 0.9, 1.0, 1.5, 2.0, 2.5, 3.0, 4.0, or 5.0 mm. Gas residence times in the bubbly liquid pool can be 1 second to 60 seconds, or less than or equal to 60 seconds and greater than or equal to 1 second, and less than, equal to, or greater than 2 seconds, 5, 10, 15, 20, 25, 30, 40, or 50 seconds.

The gas in the headspace of the apparatus used to bubble the gas into the aqueous solution (which can include the portions of the gas that is bubbled into the aqueous solution but that does not form a foam and is not captured in bubbles) can be allowed to vent to the atmosphere or ambient space, or the gas in the headspace of the apparatus can be captured. In various aspects, the captured headspace gas can be treated prior to releasing to the atmosphere or ambient space, such as via treatment with basic water to capture any volatilized PFAS compounds in the gas. For example, the method can include bubbling the headspace gas through basic water prior to releasing to the atmosphere or ambient space, such as in one or more water traps (e.g., one trap, two traps, three traps, or more). The basic water can have any suitable pH, such as a pH of 8-15, or 10-14, or less than or equal to 15 and greater than or equal to 8 and less than, equal to, or greater than 8.5, 9, 9.5, 10, 10.5, 11, 11.5, 12, 12.5, 13, 13.5, 14, or 14.5.

The gas in the generated foam can include volatilized PFAS compounds. After breaking the foam or allowing the bubbles of the foam to dissipate, the released gas from the broken or dissipated foam can be allowed to vent to the atmosphere or ambient space, or the released gas can be captured. In various aspects, the captured released gas can be treated prior to releasing to the atmosphere or ambient space, such as via treatment with basic water to capture any volatilized PFAS compounds in the gas. For example, the method can include bubbling the released gas through basic water prior to releasing to the atmosphere or ambient space, such as in one or more water traps (e.g., one trap, two traps, three traps, or more). The basic water can have any suitable pH, such as a pH of 8-15, or 10-14, or less than or equal to 15 and greater than or equal to 8 and less than, equal to, or greater than 8.5, 9, 9.5, 10, 10.5, 11, 11.5, 12, 12.5, 13, 13.5, 14, or 14.5.

The aqueous solution can be from any suitable water source. For example, the aqueous solution can include water from a natural source (e.g., a pond, lake, river, stream, or combination thereof), an extract from contaminated soil, an extract from contaminated landfill materials, water contaminated with residual fire-fighting foam, industrial waste water (e.g., residues from the manufacture of water-repellant coatings or the application of those material to fabric or other surfaces, residues from the manufacture of non-stick coatings and from the application thereof, residue from semiconductor manufacture, residue from pesticide manufacture, residue from paint manufacture, or a residue from photography), a concentrate of any one or any combination thereof, or a combination thereof. The aqueous solution can be taken directly from a water source contaminated with the fluoroalkyl compound. In other aspects, the aqueous solution is formed by concentrating the fluoroalkyl compound from feed water, wherein the feed water can be taken directly from a water source contaminated with the fluoroalkyl compound or the feed water can be a concentrated extract of the fluoroalkyl compound derived from the water source.

The aqueous solution can include an additive. The method can include adding an additive to the aqueous solution prior to or during the bubbling, or adding an additive to a feed water from which the fluoroalkyl compound in the aqueous solution is concentrated. For example, the additive can be a metal component including a metal that is added to the aqueous solution or to feed water. In various aspects, the additive can include a metal component including a metal. The metal of the metal component can be any suitable one or more metals. For example, the metal can include Mg, Al, Fe, Zn, Cu, Cd, Cr, Hg, Ni, V, Ce, or a combination thereof. The metal can include Al (e.g., $Al^{3+}$). The metal can include Mg (e.g., $Mg^{2+}$). The metal component can be $Al^{3+}$ or a compound of aluminum such as aluminum chloride or aluminum hydroxide. Adding the additive to the aqueous solution can include adding a salt of the metal of the metal component. The additive can include $AlCl_3$, $Al(OH)_3$, $AlPO_4$, $Al_2(SO_4)_3$, or a combination thereof. Adding the metal component to the aqueous solution can include adding an aqueous concentrate of the metal component to the aqueous solution. For example, adding the metal component to the aqueous solution can include adding an aqueous concentrate to the aqueous solution that includes $AlCl_3$, $Al(OH)_3$, $AlPO_4$, $Al_2(SO_4)_3$, or a combination thereof. In various aspects, the aqueous concentrate can be formed by dissolving aluminum metal in acid, such as HCl (e.g., to form an $AlCl_3$ solution). The aqueous concentrate can have a low pH, such as a pH of 0 to 4, or 0 to 3, or 0 to 2.7, or less than or equal to 4 and greater than or equal to 0 and less than, equal to, or greater than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, or 3.9. The addition of the aqueous concentrate to the aqueous solution can cause the aqueous solution to have a pH of 0 to 5.5 (e.g., the addition of the aqueous concentrate can lower the pH of the aqueous solution). Adding the metal component to the aqueous solution can include adding a metal component to the aqueous solution that is recycled from a previous iteration of the method and recovered from the clarified aqueous solution thereof. The method can optionally include acidifying (e.g., via addition of acid, such as HCl, HBr, $HNO_3$, $H_2SO_4$, $HClO_4$, $HClO_3$, or a combination thereof) or basifying (e.g., via addition of base, such as NaOH, KOH, or a combination thereof) the aqueous solution such that the aqueous solution achieves a pH of 0 to 5.5.

The addition of the metal component to the aqueous solution can include adding an aqueous solution of a salt of the metal of the metal component aqueous solution. The aqueous solution of the salt of the metal of the metal component can have any suitable concentration of the metal, such as a concentration of the metal of about 0.001 ppm to about 999,999 ppm, or about 50,000 ppm to about 140,000 ppm, or less than or equal to about 999,999 ppm and greater than or equal to about 0.001 ppm and less than, equal to, or greater than 0.001 ppm, 0.005, 0.01, 0.05, 0.1, 0.5, 1, 1.5, 2, 5, 10, 15, 20, 50, 100, 150, 200, 500, 1,000, 1,100, 1,200, 1,500, 2,000, 2,500, 5,000, 10,000, 15,000, 20,000, 50,000, 100,000, 150,000, 200,000, 500,000, 750,000, or 900,000 ppm. A volumetric ratio of the aqueous solution of the salt of the metal of the metal component added to the feed water or aqueous solution can be any suitable ratio, such as a ratio of 5:1 to 1:1000, 1:1 to 1:100, or less than or equal to 5:1 and greater than or equal to 1:1000 or less than, equal to, or greater than 1:500, 1:200, 1:100, 1:50, 1:25, 1:10, 1:8, 1:6, 1:4, 1:2, 1:1, 2:1, 3:1, or 4:1.

The metal and/or metal component can have any suitable concentration in the aqueous solution after addition of the metal and/or metal component thereto. For example, the aqueous solution can have a concentration of the metal and/or metal component of 0.01 ppm to 800 ppm, or 0.01 ppm to 600 ppm, or 1 ppm to 500 ppm, or less than or equal to 800 ppm and greater than or equal to 0.01 ppm and less than, equal to, or greater than 0.05 ppm, 0.1, 0.2, 0.4, 0.6, 0.8, 1, 2, 3, 4, 5, 6, 8, 10, 12, 14, 16, 18, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 320, 340, 360, 380, 400, 420, 440, 460, 480, 500, 520, 540, 560, 580, 600, 650, 700, or 750 ppm.

The aqueous solution can have a pH of 0 to 5.5, or 0 to 5.2, or 1 to 4.5, or less than or equal to 5.5 and greater than or equal to 0 and less than, equal to, or greater than 0.5, 1, 1.2, 1.4, 1.5, 1.6, 1.8, 2, 2.2, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, or 5.4. The method can include adding one or more acids to the aqueous solution before or during the bubbling to achieve and/or maintain the pH of 0 to 5.5. For example, the method can include adding the one or more acids to a pre-acidification aqueous solution to form the aqueous solution having a pH of 0 to 5.5. The one or more acids can include HCl, HBr, $HNO_3$, $H_2SO_4$, $HClO_4$, $HClO_3$, or a combination thereof. The one or more acids can include HCl, $H_2SO_4$, or a combination thereof.

The aqueous solution can have any suitable concentration of the fluoroalkyl compound, or of a combination of the fluoroalkyl compounds, such as a concentration of 0.001 parts-per-trillion (ppt) to 100,000 parts-per-million (ppm), or 0.001 ppt to 100 ppm, or 0.1 parts-per-billion (ppb) to 100,000 ppm, or 0.1 ppt to 100,000 ppm, or 1 ppt to 100,000 ppm, or less than or equal to 100,000 ppm and greater than or equal to 0.001 ppt and less than, equal to, or greater than 0.002 ppt, 0.003, 0.004, 0.005, 0.01, 0.05, 0.1, 0.5, 1, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppt, 1 ppb, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppb, 1 ppm, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750, 1,000, 1,500, 2,000, 5,000, 10,000, 15,000, 20,000, 40,000, 60,000, or 80,000 ppm.

The foam removed from the aqueous solution forms the concentrate that includes the foam. The concentrate is an aqueous concentrate. The removing of the foam from the aqueous solution to form the aqueous concentrate can be conducted in any suitable manner. The removing of the foam from the aqueous solution can include scooping the foam from a surface of the aqueous concentrate, vacuuming the foam from a surface of the aqueous concentrate, pushing the foam off a surface of the aqueous concentrate, or a combination thereof. The method can further include breaking the foam (e.g., substantially eliminating the gas bubbles therein), to form the aqueous concentrate. The aqueous concentrate can have a concentration of the fluoroalkyl compound from the aqueous solution, or a concentration of a combination of the fluoroalkyl compounds from the aqueous solution, that is greater than the concentration of the fluoroalkyl compound in the aqueous solution or that is greater than the concentration of a combination of the fluoroalkyl compounds in the aqueous solution. The aqueous concentrate can have a concentration of the fluoroalkyl compound from the aqueous solution, or a concentration of a combination of the fluoroalkyl compounds from the aqueous solution, of 0.005 parts-per-trillion (ppt) to 500,000 parts-per-million (ppm), or 0.005 ppt to 1,000 ppm, or less than or equal to 500,000 ppm and greater than or equal to 0.005 ppt and less than, equal to, or greater than 0.01 ppt, 0.05, 0.1, 0.5, 1, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppt, 1 ppb, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppb, 1 ppm, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750, 1,000, 1,500, 2,000, 5,000, 10,000, 15,000, 20,000, 40,000, 60,000, 80,000, 100,000, 150,000, 200,000, 300,000, or 400,000 ppm. Herein, concentration of the fluoroalkyl compound in the concentrate can be measured with the concentrate substantially free of bubbles and foam. A ratio of a concentration of the fluoroalkyl compound in the aqueous solution to a concentration of the fluoroalkyl compound in the concentrate can be 1:2 to 1:2,000,000, or 1:2 to 1:100,000, or 1:5 to 1:40, or less than or equal to 1:2 and greater than or equal to 1:2,000,000 and less than, equal to, or greater than 1:1,000,000, 1:900,000, 1:800,000, 1:700,000, 1:600,000, 1:500,000, 1:400,000, 1:300,000, 1:200,000, 1:100,000, 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, 1:5, 1:4, or 1:3. A ratio of the volume of the aqueous solution with respect to the volume of the aqueous concentrate produced therefrom can substantially correspond to the ratio of the concentration of the fluoroalkyl compound in the aqueous solution to the concentration of the fluoroalkyl compound in the aqueous concentrate. For example, the ratio of the volume of the aqueous solution with respect to the volume of the aqueous concentrate can be 1:2 to 1:2,000,000, or 1:2 to 1:100,000, or 1:5 to 1:40, or less than or equal to 1:2 and greater than or equal to 1:2,000,000 and less than, equal to, or greater than 1:1,000,000, 1:900,000, 1:800,000, 1:700,000, 1:600,000, 1:500,000, 1:400,000, 1:300,000, 1:200,000, 1:100,000, 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, 1:5, 1:4, or 1:3.

The clarified aqueous solution is the aqueous solution having the foam removed therefrom. The clarified aqueous solution has a concentration of the fluoroalkyl compound from the aqueous solution, or a concentration of a combination of the fluoroalkyl compounds from the aqueous solution, that is lower than the concentration of the fluoroalkyl compound in the aqueous solution or the concentration of the multiple fluoroalkyl compounds in the aqueous solution. The clarified aqueous solution can have a concentration of the fluoroalkyl compound of 0.0001 parts-per-trillion (ppt) to 100 parts-per-million (ppm), or 0.0001 ppt to 10 ppt, or 0.0001 ppt to 4 ppt, or less than or equal to 100 ppm and greater than or equal to 0.0001 ppt or less than, equal to, or greater than 0.0002 ppt, 0.0004, 0.0006, 0.0008, 0.001, 0.005, 0.01, 0.05, 0.1, 0.2, 0.4, 0.5, 0.6, 0.8, 1, 1.5, 2, 2.5, 3, 3.5, 4, 4.5, 5, 6, 7, 8, 9, 10, 11, 12, 13, 14, 15, 16, 17, 18, 19, 20, 25, 30, 40, 50, 60, 70, 80, 90, 100, 150, 200, 250, 300, 400, 500, 750 ppt, 1 ppb, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppb, 1 ppm, 2, 3, 4, 5, 6, 7, 8, 9, 10, 11, 12, 13, 14, 15, 20, 25, 30, 35, 40, 45, 50, 60, 70, 80, or 90 ppm. A ratio of a concentration of the fluoroalkyl compound in the clarified aqueous solution to a concentration of the fluoroalkyl compound in the aqueous solution can be 1:2 to 1:1000, or 1:5 to 1:40, or less than or equal to 1:2 and greater than or equal to 1:1,000 and less than, equal to, or greater than 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, 1:5, 1:4, or 1:3.

Figure 8:
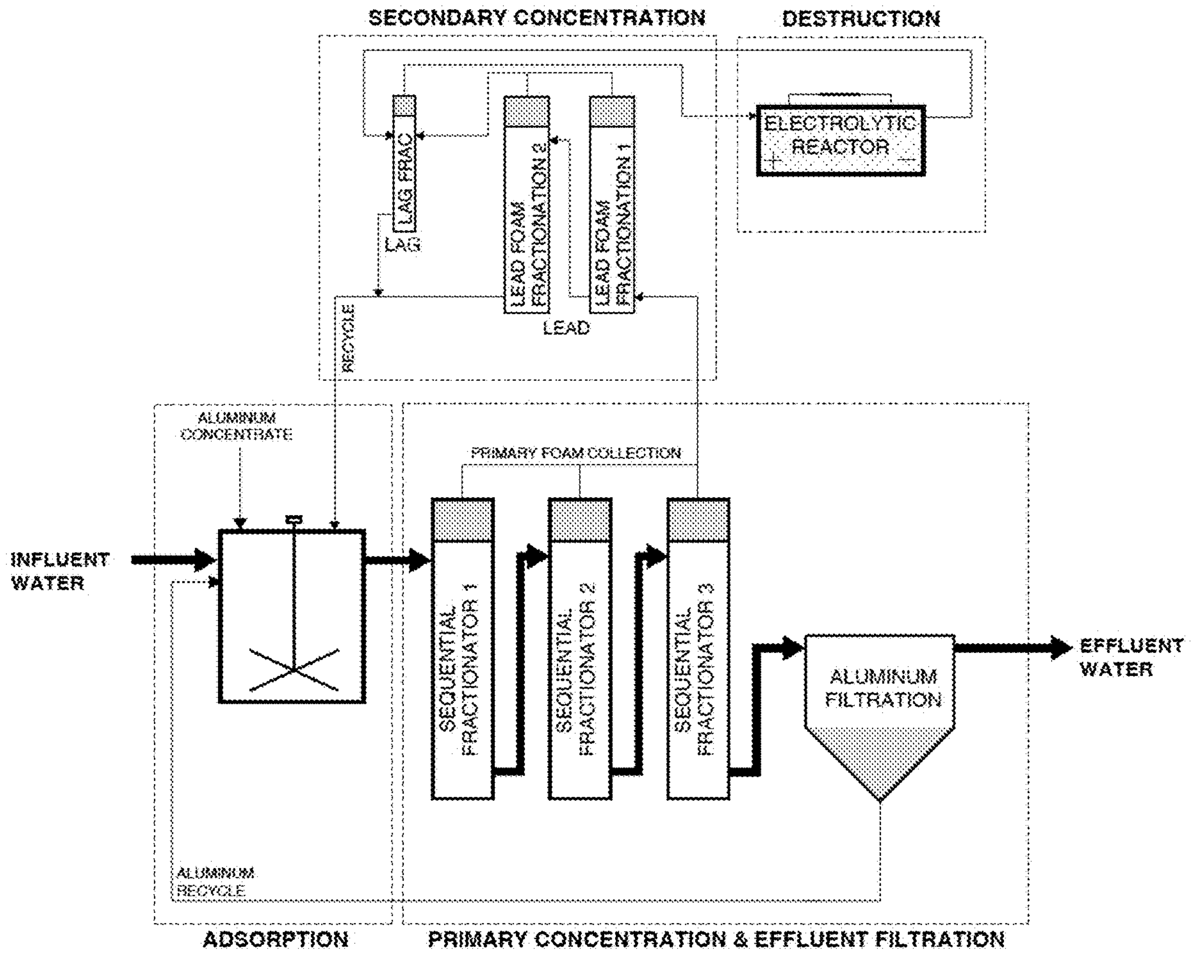
FIG. 8 illustrates a detailed process flow diagram of an apparatus used for foam separation of PFAS, in accordance with various aspects of the present invention.

The method can be performed in a batch mode, a semi-batch mode, a continuous mode, a stripping mode, or a combination thereof. In batch mode, a fixed volume of the aqueous solution can be subjected to the bubbling, foam can be generated to a desired height, gas supply can be stopped, and the foam can be allowed to drain before collection. In semi-batch mode, the aqueous solution can be charged batchwise to the apparatus while gas is sparged continuously, and foam can be collected continuously or periodically at the top of a column while the liquid pool becomes depleted over time. A secondary concentration step (e.g., bubbling gas into and removing foam from a concentrate formed from a prior iteration of bubbling and foam removal, as shown in FIG. 8) can be performed in semi-batch mode. In continuous mode, the aqueous solution can be fed continuously to the apparatus and the clarified aqueous solution is withdrawn continuously while foam is collected. A primary concentration step (e.g., bubbling gas into the aqueous solution and removing foam therefrom, as shown in FIG. 8) can be performed in continuous mode or a variation thereof. Continuous mode can include external reflux, wherein a portion of collected formate can be returned to the top of a column as wash water. In stripping mode, a feed stream can be added to the top of a foam column and stripped by rising gas. The method can include internal reflux, wherein liquid can be liberated within the column by bubble coalescence or disproportionation and flows countercurrent to the rising foam. The method can include bubble fractionation, wherein species can be concentrated toward the top of a bubbly liquid layer by adsorption to the surface of rising bubbles without the formation of a stable foam layer, and the enriched liquid near the surface can be removed.

The method can include controlling a position of an interface between a bubbly liquid zone and a foam zone in the apparatus in which the bubbling is performed. The controlling can include using one or more sensors including a pressure transducer, a level transmitter, a conductivity sensor, an optical sensor, an ultraviolet (UV) absorption sensor, or a combination thereof. The controlling can include using a feedback control loop such as a proportional-integral-derivative (PID) control loop to modulate one or more of a gas flow rate, a valve position, an outlet weir height, a liquid feed rate, a liquid withdrawal rate, or a combination thereof. The controlling can include using automated flow control valves, variable-speed pumps, or a combination thereof. Inventory control can be managed through a vented underflow arrangement, wherein the pressure of a liquid pool in the apparatus is maintained by raising the outlet level of a bottom rejectate stream using a vented T-piece, allowing for adjustment of the gauge pressure at the bottom of the column.

The method can include foaming the aqueous solution, collecting the first foam, then foaming the residual aqueous solution again and collecting the second foam. The first and second foams can be combined to form the concentrate. The residual aqueous solution having the second foam removed therefrom can be the clarified aqueous solution. The foaming of the "bottoms" can be repeated any suitable number of times to achieve a desired concentration of the fluoroalkyl compound in the clarified aqueous solution (e.g., repeated equal to, less than, or greater than 1 time, 2 times, 3, 4, 5, 6, 7, 8, 9, or 10 times). The repeated foaming of the "bottoms" is illustrated in FIG. 8 as the primary concentration step performed by sequential fractionators 1-3, wherein sequential fractionator 1 performs the first iteration, and sequential fractionators 2-3 perform the second and third iteration, respectively. For example, in various aspects, the aqueous solution having had the foam removed therefrom can be a second aqueous solution, and the method can further include bubbling the gas into the second aqueous solution to form a second foam and removing the second foam from the second aqueous solution, and combining the foam removed from the aqueous solution and the second foam to form the concentrate including the fluoroalkyl compound, and the second aqueous solution having the second foam removed therefrom can be the clarified aqueous solution. In various aspects, the second aqueous solution having had the second foam removed therefrom can be a third aqueous solution, and the method can further include bubbling the gas into the third aqueous solution to form a third foam and removing the third foam from the third aqueous solution, and combining the foam removed from the aqueous solution, the second foam, and the third foam to form the concentrate including the fluoroalkyl compound and wherein the third aqueous solution having the foam removed therefrom is the clarified aqueous solution. In various aspects, the method can include repeating sequential foaming of the aqueous solution more than two times, and combining the removed foams to form the concentrate including the fluoroalkyl compound, and wherein the sequentially foamed aqueous solution having the foams removed therefrom is the clarified aqueous solution.

The method can include performing the method once and not more than one time. In other aspects, the method can include performing the method two or more times (e.g., a first time, and a subsequent iteration), using the aqueous concentrate as the aqueous solution in each iteration of the two or more times. In an aspect including performing the method two or more times, the method can include performing the bubbling of the gas into the aqueous concentrate to form the foam and the removal of the foam to form the concentrate and the clarified aqueous solution using the concentrate from a previous iteration (e.g., first, or subsequent) of the foaming. In other words, the method can include performing the bubbling of gas into a concentrate from a previous iteration of the foaming to form the foam and removing the foam therefrom, such that the removed foam is the concentrate and the liquid having foam removed therefrom is the clarified aqueous solution. For example, the method can include performing a first iteration including bubbling a gas into an aqueous composition including the fluoroalkyl compound to form a foam including the fluoroalkyl compound, and removing the foam from the aqueous solution to form a concentrate including the fluoroalkyl compound and to form a clarified aqueous solution. The method can then include performing a second iteration including bubbling the gas into the concentrate including the fluoroalkyl compound to form a secondary foam including the fluoroalkyl compound and removing the secondary foam from the concentrate to form a secondary concentrate including the fluoroalkyl compound and to form a secondary clarified aqueous solution. Performing the bubbling and removing multiple times using the formed concentrate as the aqueous solution corresponds to the secondary concentration step shown in FIG. 8, wherein the sequential fractionators 1-3 in the primary concentration represent the first iteration, the lead foam fractionators 1-2 in the secondary concentration represent the second iteration, and the lag fractionator in the secondary concentration represent the third iteration. The method can include recycling the clarified aqueous solution formed form the second or higher iteration of the two or more times back to the aqueous solution used in the first foaming step of the method; such recycling corresponds to the recycle stream in FIG. 8 from the lead foam fractionator 2 in the secondary concentration step. During a second or higher iteration of the two or more times, a pH of the aqueous solution can be 0 to less than 4, such as 2.5 to less than 4, or less than 4 and greater than or equal to 0 and less than, equal to, or greater than 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, or 3.9. For example, in FIG. 8, the pH of the aqueous solution in the secondary concentration step can be 0 to 4. A ratio of a concentration of the fluoroalkyl compound in the aqueous solution used in the first iteration of the two or more times to a concentration of the fluoroalkyl compound in the concentrate formed by the last iteration of the two or more times can be 1:4 to 1:100,000, or 1:10 to 1:80, or less than or equal to 1:4 and greater than or equal to 1:100,000 or less than, equal to, or greater than 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, or 1:5. A ratio of the volume of the aqueous solution used in the first iteration of the two or more times to the volume of the concentrate formed by the last iteration of the method can substantially correspond to the ratio of the concentration of the fluoroalkyl compound in the aqueous solution used in the first iteration of the two or more times to the concentration of the fluoroalkyl compound in the concentrate formed by the last iteration of the two or more times. For example, the ratio of the volume of the aqueous solution used in the first iteration of the two or more times to the volume of the concentrate formed by the last iteration of the method can be 1:4 to 1:100,000, or 1:10 to 1:80, or less than or equal to 1:4 and greater than or equal to 1:100,000 or less than, equal to, or greater than 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, or 1:5.

During performance of a second or higher iteration of the bubbling and the removing of the foam using the formed concentrate as the aqueous solution of the next iteration, the method can include foaming the aqueous solution, collecting the first foam, then foaming the residual aqueous solution again and collecting the second foam. The first and second foams can be combined to form the concentrate. The residual aqueous solution having the second foam removed therefrom can be the clarified aqueous solution. The foaming of the "bottoms" from the second or higher iteration of the bubbling and the removing of the foam using the formed concentrate as the aqueous solution of the next iteration can be repeated any suitable number of times to achieve a desired concentration of the fluoroalkyl compound in the clarified aqueous solution (e.g., repeated equal to, less than, or greater than 1 time, 2 times, 3, 4, 5, 6, 7, 8, 9, or 10 times). The repeated foaming of the "bottoms" from the second or higher iteration of the bubbling and the removing of the foam using the formed concentrate as the aqueous solution of the next iteration is illustrated in FIG. 8 in the secondary concentration step as performed by lead foam fractionator 2, wherein sequential fractionators 1-3 perform the first iteration of the bubbling and removing of the foam, and wherein the concentrate therefrom then is bubbled and the foam removed in lead foam fractionator 1, and the "bottoms" from lead form fractionator 1 is then foamed in lead foam fractionator 2. The bubbling and removing of foam from the "bottoms" can be repeated more than once; for example, during the second or higher iteration of the two or more times, the second aqueous solution having had the second foam removed therefrom is a third aqueous solution, further including bubbling the gas into the third aqueous solution to form a third foam and removing the third foam from the third aqueous solution, and combining the foam removed from the aqueous solution, the second foam, and the third foam to form the concentrate including the fluoroalkyl compound and wherein the third aqueous solution having the foam removed therefrom is the clarified aqueous solution (such an embodiment would correspond to the apparatus in FIG. 8 as a lead foam fractionator 3, which is not shown). The method can include, during the second or higher iteration of the two or more times, repeating sequential foaming of the aqueous solution more than two times, and combining the removed foams to form the concentrate including the fluoroalkyl compound, and wherein the sequentially foamed aqueous solution having the foams removed therefrom is the clarified aqueous solution. The method can include recycling the clarified aqueous solution formed form the second or higher iteration of the two or more times back to the aqueous solution used in the first foaming step of the method; such recycling corresponds to the recycle stream in FIG. 8 from the lead foam fractionator 2 in the secondary concentration step.

After performance of a second or higher iteration of the bubbling and the removing of the foam using the formed concentrate as the aqueous solution of the next iteration, the concentrate formed by the second or higher iteration of the bubbling and the removing of the foam can be used as the aqueous solution in a third or higher iteration of the bubbling and the removing of the foam. Such a third iteration corresponds to the lag fractionator shown in FIG. 8, which uses the concentrate formed by lead foam fractionators 1-2 as the aqueous solution thereof. For example, the method can include performing the bubbling of the gas into the aqueous solution including the fluoroalkyl compound to form the foam including the fluoroalkyl compound and the removing of the foam from the aqueous solution to form the concentrate including the fluoroalkyl compound and to form the clarified aqueous solution one or more additional times using the concentrate formed by combining the foam and any additional foams as the aqueous solution in each of the one or more additional times. The method can include recycling the clarified aqueous solution formed from performing the bubbling of the gas into the aqueous solution including the fluoroalkyl compound to form the foam including the fluoroalkyl compound and the removing of the foam from the aqueous solution to form the concentrate including the fluoroalkyl compound and to form the clarified aqueous solution the one or more additional times back to the aqueous solution used in the first foaming step of the method; such recycling corresponds to the recycling stream in FIG. 8 shown coming from the lag fractionator.

In various aspects, the aqueous solution having had the foam removed therefrom is a second aqueous solution, and the method further includes bubbling the gas into the second aqueous solution to form a second foam and removing the second foam from the second aqueous solution, and combining the foam removed from the aqueous solution and the second foam to form the concentrate including the fluoroalkyl compound, and wherein the second aqueous solution having the second foam removed therefrom is the clarified aqueous solution; this corresponds to sequential fractionators 1-2 in FIG. 8. The method can include performing the bubbling of the gas into the aqueous solution including the fluoroalkyl compound to form the form including the fluoroalkyl compound and the removing of the foam from the aqueous solution to form the concentrate including the fluoroalkyl compound and to form a clarified aqueous solution two or more times using the concentrate as the aqueous solution in each iteration of the two or more times, wherein during a second or higher iteration of the two or more times a pH range of the aqueous solution is 0 to less than 4; this corresponds to lead foam fractionator 1 in FIG. 8. During a second or higher iteration of the two or more times, the aqueous solution having had the foam removed therefrom can be a secondary second aqueous solution, and the method can further include bubbling the gas into the secondary second aqueous solution to form a secondary second foam and removing the secondary second foam from the secondary second aqueous solution, and combining the foam removed from the aqueous solution in the first iteration of the two or more times and the secondary second foam to form the concentrate including the fluoroalkyl compound, and wherein the secondary second aqueous solution having the secondary second foam removed therefrom is a secondary clarified aqueous solution; this corresponds to lead foam fractionator 2 in FIG. 8. The method can include recycling the secondary clarified aqueous solution formed from the second or higher iteration of the two or more times back to the aqueous solution used in the first foaming step of the method; this corresponds to the recycle stream shown in FIG. 8 coming from lead foam fractionator 2.

In various aspects, the method includes one or more additional purification processes to further remove contaminants from the water. The one or more additional purification processes can be performed on a feed water including the fluoroalkyl compound to produce the aqueous solution, the one or more additional purification processes can be performed on the clarified aqueous solution, or a combination thereof. For example, in various embodiments, the removal of the foam to form the aqueous concentrate and the clarified aqueous composition can separate short-chain fluoroalkyl compounds, while the one or more additional purification processes remove other fluoroalkyl compounds and/or other contaminants.

In various aspects, the method is free of destroying the fluoroalkyl compound. In other aspects, the method includes destroying the fluoroalkyl compound. The method can include destroying the fluoroalkyl compound during the bubbling (e.g., via the use of a gas for the bubbling such as ozone). The method can include destroying the fluoroalkyl compound in the aqueous concentrate after the bubbling. The destroying can be performed in any suitable way, such as including thermal treatment, treatment with an electrolytic cell, plasma reactor, supercritical water, combustion, oxidation, chemical treatment (e.g., treatment with dimethylsulfoxide, acid, base, or a combination thereof, such as sulfuric acid, hydrochloric acid, or acid piranha solution, or such as potassium t-butoxide, sodium hydroxide, base piranha solution, or a combination thereof), or a combination thereof. The destroying can include treatment with an electrolytic cell.

The aqueous solution can be taken directly from a water source contaminated with the fluoroalkyl compound. In other aspects, the aqueous solution is formed by concentrating the fluoroalkyl compound from feed water, wherein the feed water can be taken directly from a water source contaminated with the fluoroalkyl compound or the feed water can be a concentrated extract of the fluoroalkyl compound derived from the water source. The method can include concentrating the fluoroalkyl compound from a feed water including the fluoroalkyl compound, to form the aqueous solution. The feed water can include water from a natural source (e.g., a pond, lake, river, stream, or a combination thereof), an extract from contaminated soil, an extract from contaminated landfill materials, water contaminated with residual fire-fighting foam, industrial waste water (e.g., residues from the manufacture of water-repellant coatings or the application of those material to fabric or other surfaces, residues from the manufacture of non-stick coatings and from the application thereof, residue from semiconductor manufacture, residue from pesticide manufacture, residue from paint manufacture, or a residue from photography), a concentrate of any one or any combination thereof, or a combination thereof. The feed water can have a concentration of the fluoroalkyl compound of 0.001 parts-per-trillion (ppt) to 100,000 parts-per-million (ppm), or 0.001 ppt to 100 ppm, or less than or equal to 100,000 ppm and greater than or equal to 0.001 ppt and less than, equal to, or greater than 0.002 ppt, 0.003, 0.004, 0.005, 0.01, 0.05, 0.1, 0.5, 1, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppt, 1 ppb, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750 ppb, 1 ppm, 2, 3, 4, 5, 6, 7, 8, 9, 10, 11, 12, 13, 14, 15, 20, 25, 30, 35, 40, 45, 50, 60, 70, 80, 90, 100, 150, 200, 250, 300, 400, 500, 750, 1,000, 1,500, 2,000, 5,000, 10,000, 15,000, 20,000, 40,000, 60,000, or 80,000 ppt. A ratio of a concentration of the fluoroalkyl compound in the feed water to a concentration of the fluoroalkyl compound in the aqueous solution can be 1:2 to 1:2,000,000, or 1:2 to 1:100,000, or 1:2 to 1:50, or less than or equal to 1:2 and greater than or equal to 1:2,000,000 and less than, equal to, or greater than 1:1,000,000, 1:900,000, 1:800,000, 1:700,000, 1:600,000, 1:500,000, 1:400,000, 1:300,000, 1:200,000, 1:100,000, 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, 1:5, 1:4, or 1:3. A ratio of the volume of the aqueous solution to the volume of the feed water can substantially correspond to the ratio of the concentration of the fluoroalkyl compound in the feed water to the concentration of the fluoroalkyl compound in the aqueous solution. For example, the ratio of the volume of the aqueous solution to the volume of the feed water can be 1:2 to 1:2,000,000, or 1:2 to 1:100,000, or 1:2 to 1:50, or less than or equal to 1:2 and greater than or equal to 1:2,000,000 and less than, equal to, or greater than 1:1,000,000, 1:900,000, 1:800,000, 1:700,000, 1:600,000, 1:500,000, 1:400,000, 1:300,000, 1:200,000, 1:100,000, 1:80,000, 1:60,000, 1:40,000, 1:20,000, 1:10,000, 1:5,000, 1:1,000, 1:900, 1:800, 1:700, 1:600, 1:500, 1:400, 1:300, 1:200, 1:100, 1:90, 1:80, 1:70, 1:65, 1:60, 1:55, 1:50, 1:48, 1:46, 1:45, 1:44, 1:42, 1:30, 1:38, 1:36, 1:35, 1:34, 1:32, 1:30, 1:28, 1:26, 1:25, 1:24, 1:22, 1:20, 1:18, 1:16, 1:15, 1:14, 1:12, 1:10, 1:9, 1:8, 1:7, 1:6, 1:5, 1:4, or 1:3.

The concentrating of the fluoroalkyl compound from the feed water to form the aqueous solution can be performed in any suitable way. In various aspects, the concentrating the fluoroalkyl compound from the feed water can include treatment of the feed water with a sorbent, treatment of the feed water with a metal component, treatment of the feed water with a galvanic or electrolytic cell, clarification of the feed water, filtration of the feed water (e.g., membrane filtration), flotation separation of the feed water, or a combination thereof.

In various aspects, the concentrating of the fluoroalkyl compound from the feed water can be free of adding metals to the feed water, such as free of adding Mg, Al, Fe, Zn, Cu, Cd, Cr, Hg, Ni, V, Ce, or a combination thereof. In various aspects, the feed water and the aqueous solution can be substantially free of Mg, Al, Fe, Zn, Cu, Cd, Cr, Hg, Ni, V, Ce, or a combination thereof. In various aspects, the feed water and the aqueous solution are substantially free of Mg and Al, or free of Al.

In various aspects, the concentrating the fluoroalkyl compound from the feed water can include contacting the feed water with a galvanic cell to form solids in the feed water that include a metal from an electrode of the galvanic cell. The concentrating can include removing the solids from the feed water, to form a clarified feed water and to form a feed water concentrate including the removed solids. The concentrating can also include acidifying the feed water including the removed solids to form the aqueous solution having a pH of 0 to 5.5. The acidifying can include adding HCl, HBr, $HNO_3$, $H_2SO_4$, $HClO_4$, $HClO_3$, or a combination thereof.

The galvanic cell can be any suitable type of galvanic cell. The galvanic cell includes an anode and a cathode. The galvanic is free of any externally-applied potential across the anode and the cathode. The anode can include Mg, Al, Fe, Zn, Cu, Cd, Cr, Hg, Ni, V, Ce, or a combination thereof. The anode can include Al or an Al alloy, and can be, for example, 90 wt % to 100 wt % Al (e.g., less than or equal to 100 wt % and greater than or equal to 90 wt % and less than, equal to, or greater than 91%, 92, 93, 94, 95, 96, 97, 98, or 99 wt %). The cathode has a different composition than the anode and can include Al, Zn, Fe, Cd, Ni, Sn, Pb, Cu, Ag, Co, Mn, Pd, Ag, carbon (e.g., BDD, graphite, graphene, or a combination thereof), or a combination thereof. The cathode can include Cu or a Cu alloy, and can be, for example, 90 wt % to 100 wt % Cu (e.g., less than or equal to 100 wt % and greater than or equal to 90 wt % and less than, equal to, or greater than 91%, 92, 93, 94, 95, 96, 97, 98, or 99 wt %). The cathode can include Mg, such as 90 wt % to 100 wt % Mg (e.g., less than or equal to 100 wt % and greater than or equal to 90 wt % and less than, equal to, or greater than 91%, 92, 93, 94, 95, 96, 97, 98, or 99 wt %). The galvanic cell can include an anode including Al and a cathode including Cu. The galvanic cell can include an anode including Al and a cathode including Mg. In various aspects, the galvanic cell includes more than one of the anodes and not more than one of the cathodes. In other aspects, the galvanic cell includes a plurality of the anodes and a plurality of the cathodes.

The anode and the cathode of the galvanic cell can have any suitable physical form. For example, the anode and the cathode can independently include a rod, a bar, a tube, a sheet, a plate, an inclined plate, a strip, a non-porous material, a porous material, a screen, a wire mesh, or a combination thereof. The anode and cathode can independently be rods, bars, or a combination thereof. The anode can be a strip or plate, and the cathode can be a porous material. The porous material can include a screen, a wire mesh, or a combination thereof. The anode and the cathode can physically contact one another. The anode and the cathode can include a gap therebetween, wherein the gap is 1 mm to 110 mm, or 2 mm to 30 mm, or less than or equal to 110 mm and greater than or equal to 1 mm and less than, equal to, or greater than 2 mm, 3, 4, 5, 6, 7, 8, 9, 10, 12, 14, 16, 18, 20, 22, 24, 26, 28, 30, 35, 40, 45, 50, 60, 70, 80, 90, or 100 mm. In various aspects, the anode and the cathode include a gap therebetween but contact one another in other locations. In various aspects, the anode and the cathode include a gap therebetween and are free of physical contact with one another (e.g., the gap represents the closest physical distance between the anode and the cathode).

FIG. 1 illustrates a side-view of a galvanic cell 100. The galvanic cell includes an anode 110, wherein the anode is a strip or a plate. The galvanic cell includes two cathodes 120 which are screens. The galvanic cell includes conductive connector 130 including a bolt, two washers (wherein each washer is between cathode 120 and anode 110), and a nut. The conductive connector 130 maintains a gap between the cathodes 120 and the anode 110.

Figure 2:
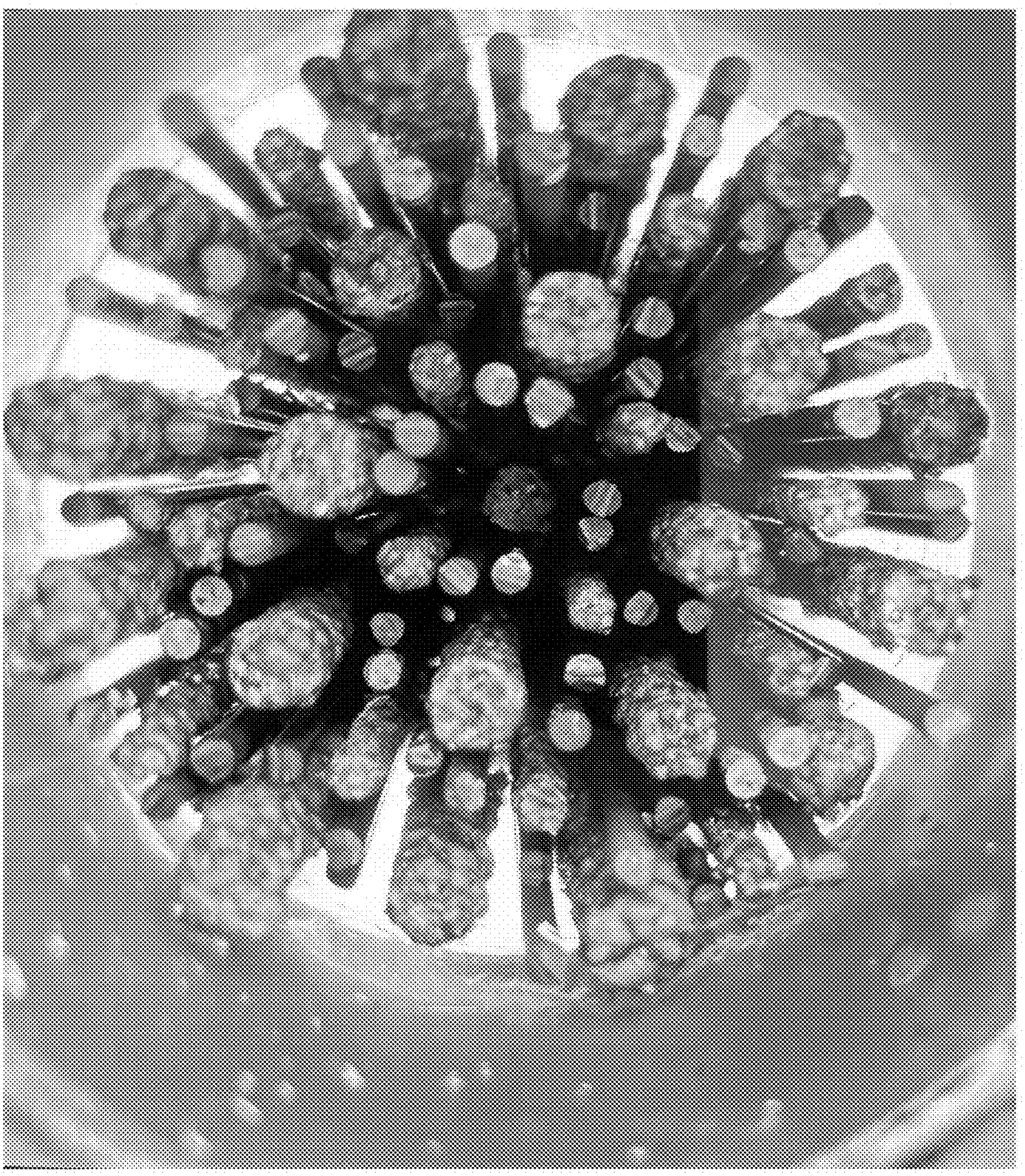
FIG. 2 illustrates a photograph showing an end of a galvanic cell in a tubular plug-flow reactor, illustrating anode and cathode rods, in accordance with various aspects.

FIG. 2 illustrates a photograph showing an end of a galvanic cell in a tubular plug-flow reactor. The photograph illustrates copper and aluminum rods. Some of the rods have a gap therebetween, while other rods are allowed to contact one another in various locations. Below the area of the photograph, the galvanic cell includes a stainless steel conductive connector in the shape of a flat puck or disc having holes therein running from one major face to the other major face that fit the rods maintain a gap between the rods at least at the location of the conductive connector.

Figure 3:
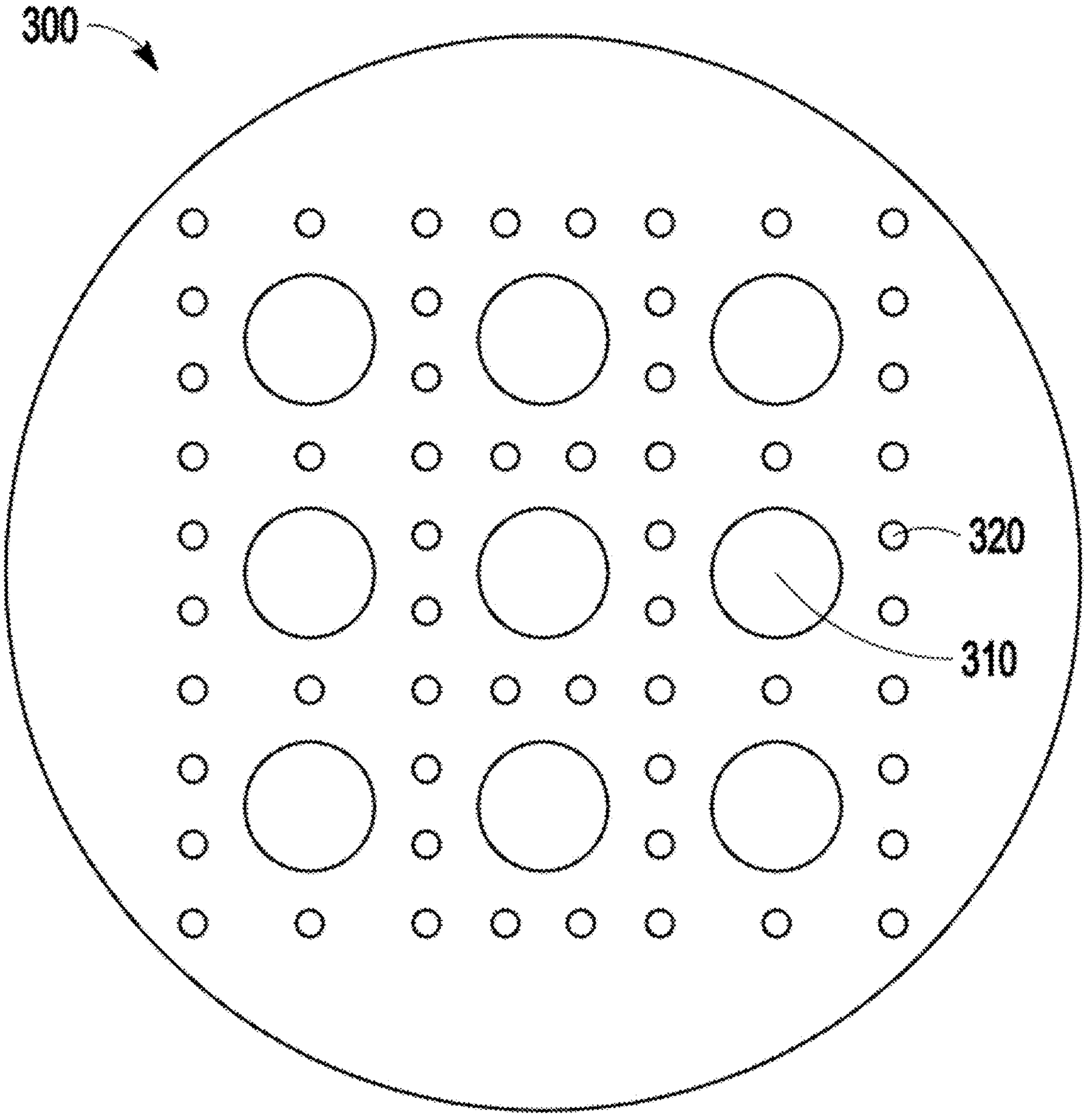
FIG. 3 illustrates schematic showing an end of a galvanic cell in a tubular plug-flow reactor, illustrating anode and cathode rods, in accordance with various aspects.

FIG. 3 illustrates schematic showing an end of a galvanic cell in a tubular plug-flow reactor, illustrating anode and cathode rods. FIG. 3 is a simplified schematic of the photograph shown in FIG. 2. FIG. 3 illustrates tubular reactor 300 having a galvanic cell therein that includes larger cathode rods 310 and smaller anode rods 320. The cathode rods 310 and the anode rods 320 include a gap therebetween.

The galvanic cell can be a tubular reactor including anode and cathode rods therein, such as aluminum rods and copper rods. The rods can be solid aluminum or copper, can be hollow rods of aluminum or copper, or can be solid or hollow rods coated or plated with aluminum or copper. The core of a plated or coated anode or cathode (e.g., the portion of the electrode underneath the plating or coating) can be any suitable electrically conductive material, such as copper, graphite, nickel, silver, titanium, brass, steel, carbon steel, stainless steel, or a combination thereof. The rods can be welded together at one or more locations along the length of the reactor. For example, the rods can be welded together at or near one or both ends of the reactor. In an example, the ends of the rods are welded together at one or both ends of the tubular reactor. The one or more welds at each location along the length of the reactor can be an electrically conductive connector that physically and electrically connects the anode and cathode rods. At the location of the weld, the anode and cathode rods can be physically contacting one another, can have a gap between one another, or a combination thereof. At locations along the length of the tubular reactor away from the one or more welds, the anode and cathode rods can be physically contacting one another, can have a gap between one another, or a combination thereof. Welds that include physical contact between anode and cathode rods can maintain contact of the rods such along a length of the reactor or proximate to the weld. Welds that include a gap between anode and cathode rods can maintain a gap between the anode and cathode, such as along a length of the reactor or proximate to the weld. Tubular reactors with a weld that includes a gap between anode and cathode rods can include contact between the anode and cathode rods at one or more locations along the length of the reactor, such as at one or more locations away from the weld.

The anode and/or cathode can be free of plated coatings of deposited metals thereon. In other aspects, the anode and/or cathode includes a plating and/or deposition thereon including Mg, Al, Fe, Zn, Cu, Cd, Cr, Hg, Ni, V, Ce, Sn, Pb, Ag, Co, Mn, Pd, Mo, carbon (e.g., BDD, graphite, graphene, or a combination thereof), or a combination thereof. A plating can be a continuous coating of the metal thereon. A deposition (e.g., chemical vapor deposition, physical vapor deposition, electrodeposition, electroless deposition, chemical reduction, or a combination thereof) can form a discontinuous coating of the deposited metal thereon. For example, in electroless deposition, a solution of the desired metal ion can be contacted for a brief period (e.g., 30 sec to 1 min) with the anode or the cathode such that the metal ion is deposited onto the surface of the contacted electrode. In various aspects, the anode can include a plating or deposition of a metal thereon, wherein the plated and/or deposited metal is a cathode or is the cathode; the deposited or plated cathode on the anode can be the only cathode in the galvanic cell (e.g., an electroless configuration), or the galvanic cell can further include another cathode that is not plated or deposited on the anode and that includes Al, Zn, Fe, Cd, Ni, Sn, Pb, Cu, Ag, Co, Mn, Pd, Ag, carbon (e.g., BDD, graphite, graphene, or a combination thereof), or a combination thereof. In various aspects, the anode includes Cu plated and/or deposited onto a surface thereof, wherein the cathode includes Cu and wherein the cathode is not plated or deposited on the anode including Al. The core of a plated or coated anode or cathode (e.g., the portion of the electrode underneath the plating or coating) can be any suitable electrically conductive material, such as copper, graphite, nickel, silver, titanium, brass, steel, carbon steel, stainless steel, or a combination thereof.

In various aspects, the galvanic cell can include a conductive connector. The conductive connector can physically and electrically connect the anode and the cathode. The conductive connector can maintain a gap between the anode and the cathode (e.g., the conductive connector can hold the anode and the cathode apart to maintain the gap therebetween), or the conductive connector can hold the anode and the cathode in contact with one another. The conductive connector can include any suitable electrically conductive material. The conductive connector can include Cu, Zn, Fe, Cd, Ni, Sn, Pb, or a combination thereof. The conductive connector can include brass, stainless steel, or a combination thereof. The conductive connector can include any suitable physical form, such as a weld, a fastener, a fastener assembly, a threaded fastener, a screw, a bolt, a bracket, a nut, a washer, or a combination thereof. The anode and cathode can include one or more suitably-sized through-holes to allow the conductive connector to pass therethrough (e.g., holes for a fastener, screw, or bolt).

The galvanic cell can include a nonconductive connector that physically connects the anode and the cathode but that does not provide an electrical connection between the anode and the cathode. The nonconductive connector can include any suitable non-electrically conductive material, such as plastic, glass, rubber, or a combination thereof, and/or wherein the nonconductive connector includes a conductive connector coated with a non-conductive material. The nonconductive connector includes a weld, a fastener, a fastener assembly, a threaded fastener, a screw, a bolt, a bracket, a nut, a washer, or a combination thereof. In various aspects, the galvanic cell includes no conductive connectors or nonconductive connectors. In various aspects, the galvanic cell includes conductive connectors but is free of nonconductive connectors. In various aspects, the galvanic cell includes nonconductive connectors and is free of conductive connectors. In various aspects, the galvanic cell includes a combination of conductive connectors and nonconductive connectors.

The concentrating the fluoroalkyl compound from the feed water can include treating the feed water with a metal component including a metal. The concentrating can include removing solids including the metal component from the feed water, to form a clarified feed water and to form a feed water concentrate including the removed solids. The solids can include contaminants from the feed water. The concentrating can also include acidifying the feed water concentrate to form the aqueous solution having a pH of 0 to 5.5. The acidifying can include adding HCl, HBr, $HNO_3$, $H_2SO_4$, $HClO_4$, $HClO_3$, or a combination thereof. The metal of the metal component can include Mg, Al, Fe, Zn, Cu, Cd, Cr, Hg, Ni, V, Ce, or a combination thereof. The metal of the metal component can include Al.

The metal of the metal component can be any suitable one or more metals. For example, the metal can include Mg, Al, Fe, Zn, Cu, Cd, Cr, Hg, Ni, V, Ce, or a combination thereof. The metal can include Al (e.g., $Al^{3+}$). The metal can include Mg (e.g., $Mg^{2+}$). The metal component can be $Al^{3+}$ or a compound of aluminum such as aluminum chloride or aluminum hydroxide. The addition of the metal component to the feed water or aqueous solution can include adding a salt of the metal of the metal component. The salt of the metal can be any suitable salt, such as $AlCl_3$, $Al(OH)_3$, $AlPO_4$, $Al_2(SO_4)_3$, or a combination thereof. The addition of the metal component can include adding an aqueous solution of a salt of the metal of the metal component to the feed water or aqueous solution. The aqueous solution of the salt of the metal of the metal component can have any suitable concentration of the metal, such as a concentration of the metal of about 0.001 ppm to about 999,999 ppm, or about 50,000 ppm to about 140,000 ppm, or less than or equal to about 999,999 ppm and greater than or equal to about 0.001 ppm and less than, equal to, or greater than 0.001 ppm, 0.005, 0.01, 0.05, 0.1, 0.5, 1, 1.5, 2, 5, 10, 15, 20, 50, 100, 150, 200, 500, 1,000, 1,100, 1,200, 1,500, 2,000, 2,500, 5,000, 10,000, 15,000, 20,000, 50,000, 100,000, 150,000, 200,000, 500,000, 750,000, or 900,000 ppm. A volumetric ratio of the aqueous solution of the salt of the metal of the metal component added to the feed water or aqueous solution can be any suitable ratio, such as a ratio of 5:1 to 1:1000, 1:1 to 1:100, or less than or equal to 5:1 and greater than or equal to 1:1000 or less than, equal to, or greater than 1:500, 1:200, 1:100, 1:50, 1:25, 1:10, 1:8, 1:6, 1:4, 1:2, 1:1, 2:1, 3:1, or 4:1. In various aspects, the metal of the metal component is produced by a galvanic or electrolytic cell (e.g., a galvanic or electrolytic cell that contacts the feed water), or the metal is produced by other than a galvanic or electrolytic cell (e.g., produced via direct addition of an aluminum salt, or via other means).

When concentrating the fluoroalkyl compound from the feed water via contacting with a galvanic cell and/or via contacting with a metal component, the clarified aqueous solution formed by removing the foam from the aqueous solution can include a metal from the electrode of the galvanic cell and/or the metal of the metal component. The method can include recycling the metal from the electrode or the metal component that is in the clarified aqueous solution. The recycling can include reusing the metal from the electrode or the metal of the metal component in the aqueous solution in a subsequent iteration of the method, such as via flowing the metal in a recycle stream to contact the aqueous solution used in the subsequent iteration of the method, or via flowing the metal in the recycle stream to contact the feed water from which the fluoroalkyl compound of the aqueous solution is concentrated in the subsequent iteration of the method. The method can include purging one or more contaminants from the recycle stream, such as contaminants including ions from the acidification of the aqueous solution which can build up in the system.

The method can include adding an additive to the aqueous solution prior to or during the bubbling, or adding an additive to a feed water from which the fluoroalkyl compound in the aqueous solution is concentrated. For example, the additive can be a metal or metal salt generated by contacting the feed water with a galvanic cell, or the additive can be a metal component including a metal that is added to the feed water. In various aspects, the additive can include a metal component including a metal, wherein the metal can include Mg, Al, Fe, Zn, Cu, Cd, Cr, Hg, Ni, V, Ce, or a combination thereof. The metal of the metal component can include Al. The additive can include $AlCl_3$, $Al(OH)_3$, $AlPO_4$, $Al_2(SO_4)_3$, or a combination thereof.

The clarified aqueous solution formed by removing the foam from the aqueous solution can include the additive. In various aspects, the method can include reusing the additive in the clarified aqueous solution and/or a metal from the additive in the clarified aqueous solution in the additive in a subsequent iteration of the method. The reusing of the additive and/or the metal therefrom can include flowing a recycle stream including at least part of the clarified aqueous solution or an extract thereof to the aqueous solution of the subsequent iteration of the method or to a feed water from which the fluoroalkyl compound in the aqueous solution is concentrated of the subsequent iteration of the method.

The reusing of the additive and/or the metal therefrom can include purging one or more acidification contaminants from the additive and/or the metal therefrom prior to the reuse of the additive and/or metal therefrom in the subsequent iteration of the method. The purging can include purging the one or more acidification contaminants from a recycle stream including at least part of the clarified aqueous solution or an extract thereof prior to the reuse of the additive and/or metal therefrom in the subsequent iteration of the method. The purging can include separating sulfate, chloride, or a combination thereof, from the additive and/or metal therefrom. The method can include adding a base to a recycle stream including at least part of the clarified aqueous solution or an extract thereof to raise a pH thereof to 3 to 6, filtering out a precipitated salt including the one or more acidification contaminants from the recycle stream, and adding the filtered recycle stream to the aqueous solution or a feed water from which the fluoroalkyl compound in the aqueous solution is concentrated. The method can include adding a base to a recycle stream including at least part of the clarified aqueous solution or an extract thereof to raise a pH thereof to 3 to 6, and filtering out a precipitated salt including the additive from the recycle stream, and adding the precipitated salt to the aqueous solution or a feed water from which the fluoroalkyl compound in the aqueous solution is concentrated.

In various aspects, concentration and removal of fluoroalkyl compounds from water can be conducted as a series of stages, including treatment of the feed water with the metal component which can collect the fluoroalkyl compound on the surface of particles such as aluminum hydroxide particles. The particles can then be separated (e.g., via sedimentation and/or filtration) to form an aqueous concentrate that contains a majority of the fluoroalkyl compounds (e.g., 90% or more). The aqueous concentrate can then be dewatered (e.g., in a mechanical press or similar device). Next, the dewatered solids can be dissolved at low pH (e.g., pH of 0 to 5.5, or 1 to 4.5) by adding an acid such as HCl and/or $H_2SO_4$ and to form the aqueous solution having a high concentration of metal ions such as aluminum ions. In the acidic aqueous solution, the fluoroalkyl compounds can be dissociated in the aqueous phase with the acid (neutral species) in equilibrium with their conjugate base (ionic species) ($C_nF_mCOOH \longleftrightarrow C_nF_mCOO^- + H^+$). The relationship between the concentrations of the two fluoroalkyl compound species (acid vs. conjugate base) is determined by the pH value. The equilibrium can be driven toward the acid species at low pH (e.g., pH of 2-3). The acid species (neutral species) can have significantly enhanced hydrophobicity which can favor increased concentration of the acid species at the water-air interface.

Under these conditions, the acid species of the fluoroalkyl compound can move easily with the addition of air or gas bubbles to the interfacial region so as to create a foam layer containing a majority (e.g., approximately 99.99% or more) of the molecules of the fluoroalkyl compound. Removal of the foam from the aqueous solution can result in a preferential concentration (e.g., into $\frac{1}{10}^{th}$ its original volume), such that destruction of the fluoroalkyl compound (e.g., via an electrochemical process, or other process) can become more efficient and economically viable. The clarified aqueous solution formed by removing the foam from the aqueous solution can have a high concentration of metal (e.g., aluminum or aluminum compounds) and/or metal ions (e.g., aluminum ions) that can be recovered, reused, and recycled back for reuse in the method by adding at least part of the clarified aqueous solution or an extract thereof to the feed water.

In various aspects, all or a portion of the clarified aqueous solution can be recycled for reuse of the metal of the metal component. For any non-recycled portions, if there are no environmental limitations on the concentration of metal component that can be reintroduced, the clarified aqueous solution enriched with the metal component can be dosed into the product water. For environmental considerations the pH can be increased with a base (e.g., sodium hydroxide, such as to pH of 3.5-4) to precipitate solid aluminum particles. At increased pH (e.g., 3.5-4), the metal component can exist in the form of polymers (e.g., aluminum-containing polymers) having high adsorption capacity and a composition similar to particles formed by the treatment of the feed water with the metal component.

In embodiments wherein the metal component is added to the feed water or aqueous solution, the clarified aqueous solution can include the metal component, such as an aluminum ion and/or aluminum hydroxide. The method can further include recycling the metal component such as including combining the feed water and the clarified aqueous solution. In some examples, the metal and/or metal component (e.g., aluminum hydroxide) can be settled (e.g., using a settling tank) and/or filtered from the clarified aqueous solution, and the settled and/or filtered metal and/or metal component can be added back to the aqueous solution. Prior to recovery of the metal and/or metal component (e.g., via settling and/or filtration) for recycling, the clarified aqueous solution can be basified to increase precipitation/sedimentation of the metal and/or metal component, such as to a pH of 5.5 to 7.5, or 6 to 7, or less than or equal to 7.5 and greater than or equal to 5.5 and less than, equal to, or greater than 5.6, 5.7, 5.8, 5.9, 6, 6.1, 6.2, 6.3, 6.4, 6.5, 6.6, 6.7, 6.8, 6.9, 7, 7.1, 7.2, 7.3, or 7.4. Basification can include adding one or more bases to the clarified aqueous solution, such as NaOH, KOH, or a combination thereof. After recovery of the metal and/or metal component (e.g., after settling and/or filtration), the recovered metal and/or metal component (which can include some amount of residual clarified aqueous solution) can be acidified to increase the solubility of the metal and/or metal component, such as to a pH of 0 to 4.5, or 0 to 4, or less than or equal to 4.5 and greater than or equal to 0 and less than, equal to, or greater than 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, or 4.4. The acidification can include the addition or one or more acids, such as HCl, HBr, $HNO_3$, $H_2SO_4$, $HClO_4$, $HClO_3$, or a combination thereof. The acidified residual clarified aqueous solution having the metal and/or metal component therein can be added to the aqueous solution to recycle the metal and/or metal component to the aqueous solution for a subsequent iteration of the bubbling and foam removal.

In various aspects, the recycling the metal of the metal component can further include purging one or more acidification contaminants from the clarified aqueous solution prior to combining the feed water and the clarified aqueous solution. In some embodiments that include destruction of the fluoroalkyl compound, such as including destruction via treatment with an electrolytic cell, the destroying the fluoroalkyl compound in the aqueous concentrate can form a liquid including the metal component, and the method can further include recycling the metal component including combining the feed water and the liquid including the metal component. The recycling can further include purging one or more acidification contaminants from the liquid including the metal component prior to combining the feed water and the liquid including the metal component. In various aspects, the clarified aqueous solution and the liquid including the metal component can be combined to form a recycle stream that is subjected to the purging of acidification contaminants.

The purging can include removing one or more contaminant ions from the liquid including the metal component and/or from the clarified aqueous solution or an extract thereof, wherein the one or more contaminant ions are from the acidification to form the aqueous solution having a pH of 0 to 5.5. The purging can include removing sulfate, chloride, or a combination thereof, from the liquid including the metal component. The purging can reduce or eliminate build-up of contaminants added to the recycle loop via the acidification step, such as sulfate from sulfuric acid or chloride from hydrochloric acid.

The purging can include raising a pH of the liquid including the metal component and/or from the clarified aqueous solution or an extract thereof to 3 or less (e.g., 1 to 3, or 2 to 3, or less than or equal to 3 and greater than or equal to 1 and less than, equal to, or greater than 1.1, 1.2, 1.3, 1.4, 1.5, 1.6, 1.7, 1.8, 1.9, 2, 2.1, 2.2, 2.3, 2.4, 2.5, 2.6, 2.7, 2.8, or 2.9) and filtering out a salt of the one or more contaminant ions from the liquid including the metal component and/or from the clarified aqueous solution or an extract thereof. The purging can include raising a pH of the liquid including the metal component and/or from the clarified aqueous solution or an extract thereof to 3 or less and filtering solid aluminum sulfate therefrom. The purging can include raising a pH of the liquid including the metal component and/or from the clarified aqueous solution or an extract thereof to 4 or less (e.g., 3.5 or less, or 1 to 4, or 1 to 3.5, or less than or equal to 3 and greater than or equal to 1 and less than, equal to, or greater than 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, or 3.9), filtering a solid salt of the metal of the metal component therefrom, and combining the solid salt of the metal of the metal component with the feed water or dissolving the solid salt in water prior to adding to the feed water. The purging can include raising a pH of t the liquid including the metal component and/or from the clarified aqueous solution or an extract thereof to 4 or less, or 3.5 or less, filtering aluminum chloride therefrom, and combining the solid salt of the metal of the metal component with the feed water or dissolving the solid salt in water prior to adding to the feed water. The purging can occur continuously or periodically, which can be determined based on a concentration measurement of the contaminant in the recycle stream.

In the case of excess sulfate, the recycle stream (which can include the liquid including the metal component and/or from the clarified aqueous solution or an extract thereof) can be partially neutralized with a base (e.g., calcium hydroxide) to a pH of approximately but not exceeding 3, which can cause the sulfate to precipitate as calcium sulfate which can then be filtered and removed from the system. In the case of excess chloride, the pH of the recycle stream can be elevated using sodium hydroxide to a pH not exceeding 3.5 to 4. In this case, the metal ion itself (e.g., Al) precipitates and can be filtered and returned to the system. The pH 3.5-4 liquid can be blended with the product water at a suitable rate.

Figure 4:
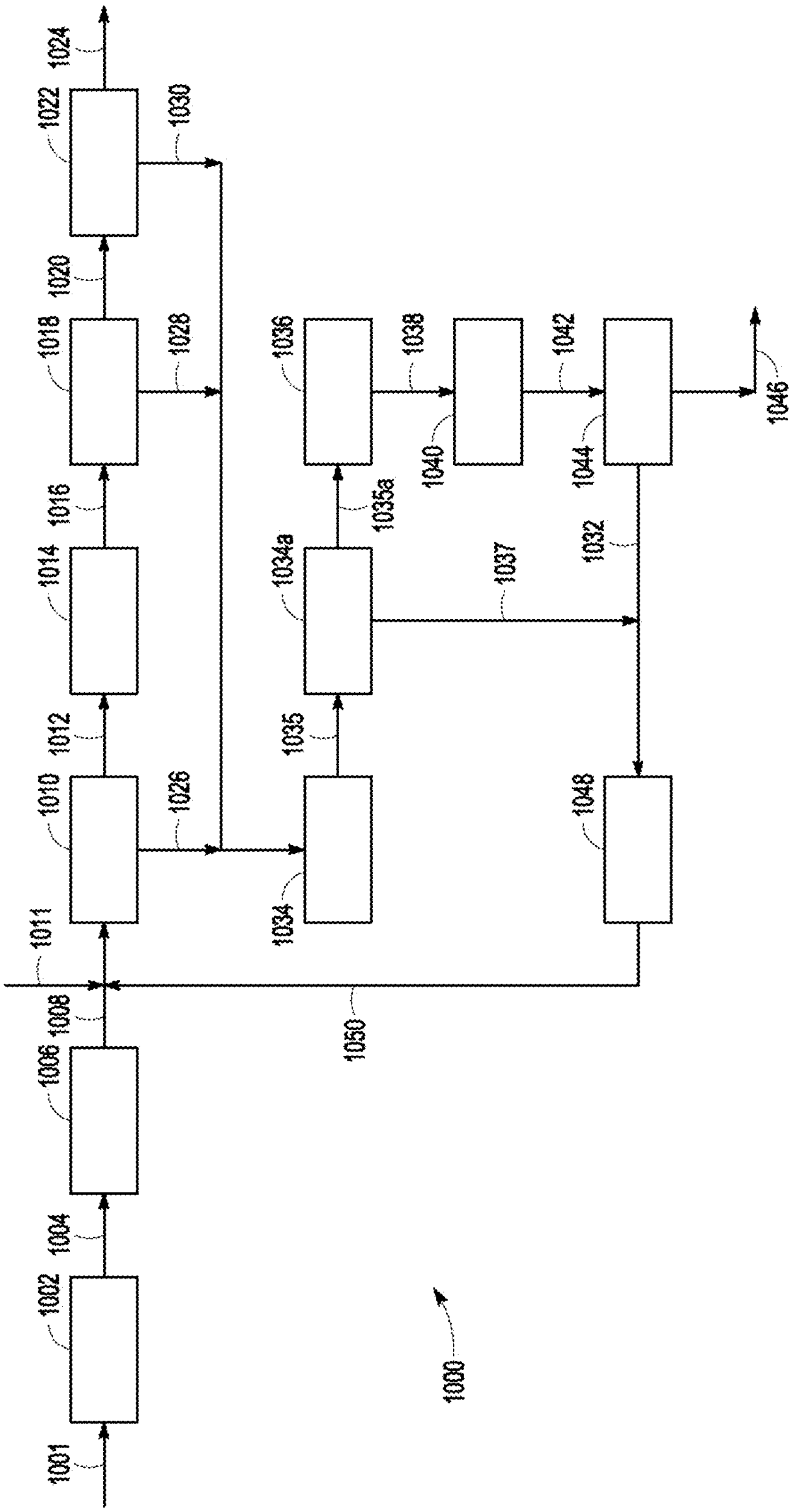
FIG. 4 illustrates a block flow diagram showing a method of treating contaminated water, in accordance with various aspects of the present invention.

FIG. 4 illustrates a block flow diagram showing a method of treating feed water 1000. The method can include subjecting feed water 1001 including a fluoroalkyl compound to a pretreatment including basification 1002 (e.g., addition of NaOH to bring pH to about 10.5) to produce basified feed water 1004. The method can include subjecting basified feed water 1004 to nitrogen removal 1006 (e.g., addition of sodium hypochlorite to remove nitrogen as ammonia) to produce feed water having nitrogen removed therefrom 1008. The feed water having nitrogen removed therefrom 808 can optionally have a metal component added thereto (e.g., in the form of dissolved aluminum ions, an aluminum-containing salt that absorbs the fluoroalkyl compound such as aluminum hydroxide, or a combination thereof) via stream 1011. The feed water 1008 is combined with aluminum ions from stream 1032 (e.g., in the form of dissolved aluminum ions, an aluminum-containing salt that absorbs the fluoroalkyl compound such as aluminum hydroxide, or a combination thereof), which forms a solid (e.g., a precipitated solid, a flocculated solid, a solid resulting from addition of a solid including the metal component to the water, or a combination thereof) that includes the metal component-treated fluoroalkyl compound. The feed water 1008 is subjected to a separation process 1010 to produce feed water 1012 and solid 1026. During or prior to separation process 1010, a polymer can be added, such as a flocculating polymer, such as a cationic polymer, a natural polymer, a synthetic polymer, a cationic polysaccharide, a gum, alginic acid, cellulose, a cellulose derivative, dextran, glycogen, a polyelectrolyte, a polymer including a quaternary ammonium group, poly(diallyl dimethyl ammonium chloride) (polyDADMAC), or a combination thereof. In step 1014, feed water 1012 can be contacted with a galvanic cell (e.g., including an anode that includes aluminum and a cathode that includes copper) to produce galvanic cell-treated water 1016 that includes a galvanic cell-treated fluoroalkyl compound. Alternatively, a galvanic cell treatment step can be absent from step 1014, and step 1014 includes a tank or other container for allowing production of the metal component-treated fluoroalkyl compound, such as for allowing the aluminum ion and the fluoroalkyl compound to react, or for allowing the aluminum ion to precipitate a salt that absorbs the fluoroalkyl compound, or for allowing an aluminum salt such as aluminum hydroxide to absorb the fluoroalkyl compound. Prior to or during step 1014, the method can include adding to the feed water HCl (e.g., to bring pH to about 5.5) and/or adding $H_2O_2$. The method can include separating 1018 the treated fluoroalkyl compound (e.g., galvanically treated, metal ion-treated, or a combination thereof) from the water 1016 to form clarified feed water 1020 having a lower concentration of the fluoroalkyl compound than the feed water 1001 (or clarified aqueous composition 1012) and to form a feed water concentrate 1028 having a higher concentration of the treated fluoroalkyl compound than the clarified feed water. The method can include posttreatment of the clarified feed water 1020 (e.g., filtration, such as ultrafiltration) to form posttreated feed water 1024 and solids 1030. The solid contaminants 1026 and solids 1030 can be combined with feed water concentrate 1028. The feed water concentrate can be subjected to conditioning 1034 (e.g., addition of $H_2SO_4$ or HCl to bring pH to about 0 to 5.5) to form aqueous solution 1035. The aqueous solution 1035 can be subjected to aeration/foaming **1034*a* to form the clarified aqueous solution 1037, and to form the aqueous concentrate 1035*a* (which is formed from the foam removed from the aqueous solution). The clarified aqueous solution 1037 can include the metal component, such as aluminum ions and/or aluminum hydroxide. The clarified aqueous solution can be combined with liquid stream 1032 for recycling of the metal component back to the feed water. The aqueous concentrate 1035*a* can be subjected to contacting with an electrolytic cell 1036 to destroy the treated fluoroalkyl compound and to form electrolytically treated aqueous composition 1038. The electrolytically treated aqueous composition 1038 can be subjected to conditioning (e.g., addition of NaOH or $Ca(OH)_2$ to bring to about 6.5-7 pH, and addition of flocculating polymer) to form conditioned electrolytically treated aqueous composition 1038, which can be subjected to separation 1044 (e.g., filtration) to form a liquid 1032 and a solid 1046. The solid contains the destroyed fluoroalkyl compound. The liquid 1032, which can include the metal component such as aluminum ions and/or aluminum hydroxide, can be subjected to purging 1048 to remove one or more acidification contaminants from the water (e.g., sulfate and/or chloride). After purging, the liquid 1050 (which includes the metal component, such as aluminum ions and/or aluminum hydroxide) can be added to the feed water, such as prior to separation 1010**.

Figure 5:
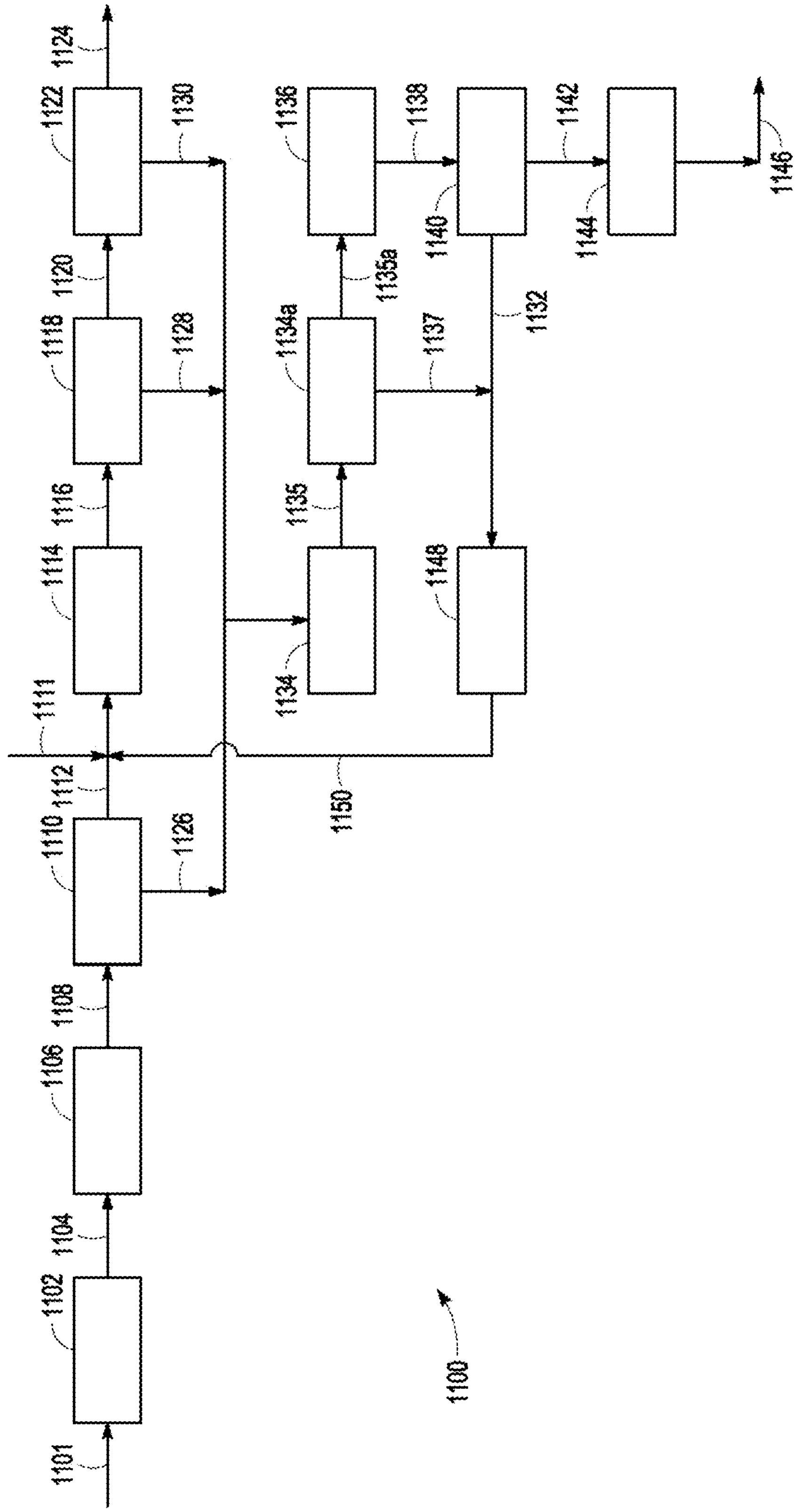
FIG. 5 illustrates a block flow diagram showing a method of treating contaminated water, in accordance with various aspects of the present invention.

FIG. 5 illustrates a block flow diagram showing a method of treating feed water 1100. The method can include subjecting feed water 1101 including a fluoroalkyl compound to a pretreatment including basification 1102 (e.g., addition of NaOH to bring pH to about 10.5) to produce basified feed water 1104. The method can include subjecting basified feed water 1104 to nitrogen removal 1106 (e.g., addition of sodium hypochlorite to remove nitrogen as ammonia) to produce feed water having nitrogen removed therefrom 1108. The feed water having nitrogen removed therefrom 1108 can optionally have a metal component added thereto (e.g., in the form of dissolved aluminum ions, an aluminum-containing salt that absorbs the fluoroalkyl compound such as aluminum hydroxide, or a combination thereof) via stream 1111. The feed water 1108 is combined with metal component from stream 1132 (e.g., in the form of dissolved aluminum ions, an aluminum-containing salt that absorbs the fluoroalkyl compound such as aluminum hydroxide, or a combination thereof), which forms a solid (e.g., a precipitated solid, a flocculated solid, a solid resulting from addition of a solid including the metal of the metal component to the water, or a combination thereof) that includes the metal component-treated fluoroalkyl compound. The feed water 1108 is subjected to a separation process 1110 to produce feed water 1112 and solid 1126. During or prior to separation process 1110, a polymer can be added, such as a flocculating polymer. In step 1114, feed water 1112 can be contacted with a galvanic cell (e.g., including an anode that includes aluminum and a cathode that includes copper) to produce galvanic cell-treated water 1116 that includes a galvanic cell-treated fluoroalkyl compound. Alternatively, a galvanic cell treatment step can be absent from step 1114, and step 1114 includes a tank or other container for allowing production of the aluminum-treated fluoroalkyl compound, such as for allowing the metal component and the fluoroalkyl compound to react, or for allowing the aluminum ion and/or aluminum hydroxide to precipitate a salt that absorbs the fluoroalkyl compound, or for allowing an aluminum salt such as aluminum hydroxide to absorb the fluoroalkyl compound. Prior to or during step 1114, the method can include adding to the clarified aqueous composition HCl (e.g., to bring pH to about 5.5) and/or adding $H_2O_2$. The method can include separating 1118 the treated fluoroalkyl compound (e.g., galvanically treated, metal ion-treated, or a combination thereof) from the water 1116 to form clarified feed water 1120 having a lower concentration of the fluoroalkyl compound than the feed water 1101 (or clarified aqueous composition 1112) and to form a feed water concentrate 1128 having a higher concentration of the treated fluoroalkyl compound than the clarified feed water. The method can include posttreatment of the clarified feed water 1120 (e.g., filtration, such as ultrafiltration) to form posttreated feed water 1124 and solids 1130. The solid contaminants 1126 and solids 1130 can be combined with feed water concentrate 1128. The feed water concentrate can be subjected to conditioning 1134 (e.g., addition of $H_2SO_4$ of HCl to bring pH to about 0 to 5.5) to form aqueous solution 1135. The aqueous solution 1135 can be subjected to aeration/foaming **1134*a* to form the clarified aqueous solution 1137, and to form the aqueous concentrate 1135*a*. The clarified aqueous solution 1137 can include the metal component such as aluminum ions and/or aluminum hydroxide. The clarified aqueous solution can be combined with liquid stream 1132 for recycling of the metal component back to the feed water. The aqueous concentrate 1135***a* can be subjected to contacting with an electrolytic cell 1136 to destroy the treated fluoroalkyl compound and to form electrolytically treated aqueous composition 1138. The electrolytically treated aqueous composition 1138 can be subjected to separation 1140 (e.g., filtration) to form a liquid 1132 and a solid 1142. The liquid 1132, which can include the metal component such as aluminum ions and/or aluminum hydroxide, can be subjected to purging 1148 to remove one or more acidification contaminants from the water (e.g., sulfate and/or chloride). The purged liquid 1150, which can include the metal component such as aluminum ions and/or aluminum hydroxide, can be added to the feed water, such as after separation 1110 and prior to step 1112. The solid can be subjected to conditioning (e.g., addition of NaOH or $Ca(OH)_2$ to bring to about 6.5-7 pH) to form solid 1146, which contains the destroyed fluoroalkyl compound.

In FIG. 4, some aluminum is lost due to basification and flocculation of the electrolytically treated aqueous composition prior to removal of the liquid therefrom. The lost aluminum represents a significant cost of operation both in terms of the cost of aluminum as well as additional disposal costs. In FIG. 5, a substantially lower amount of aluminum is lost, due to recycling of the liquid phase of the electrolytically treated aqueous composition prior to basification thereof.

EXAMPLES

Various embodiments of the present invention can be better understood by reference to the following Examples which are offered by way of illustration. The present invention is not limited to the Examples given herein.

Example 1. Foam Separation of PFAS

Figure 6:
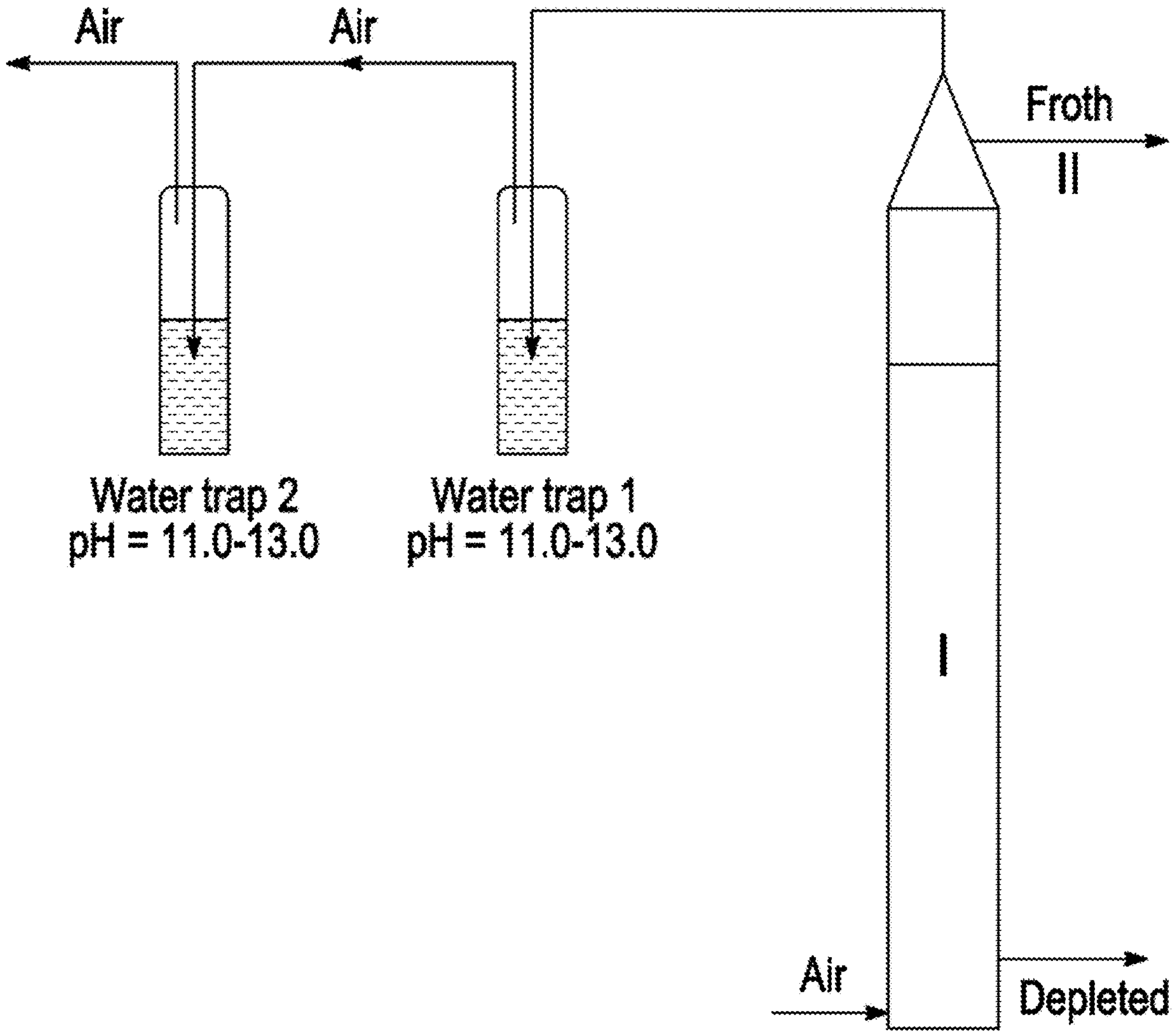
FIG. 6 illustrates an apparatus for performing a method of concentrating a fluoroalkyl compound, in accordance with various aspects of the present invention.

FIG. 6 illustrates an apparatus for performing a method of concentrating a fluoroalkyl compound. Body I refers to a lower portion of a fractionator where the water containing PFAS was initially placed, through which air was passed to concentrate the PFAS in the upper part (Body II) in froth formed by the bubbling air. The bottom water at the lower portion of the fractionation process is called "depleted". Water traps were used to collect compounds evaporating in air leaving the top of Body II using water with a pH value between 11.0-13.0. In all experiments, treatment plant (Glendale) wastewater was used at pH 2.0, with an initial spike of PFNA, PFOA, PFOS, PFHxS, and PFBS. Masses of PFAS compounds were determined using LC-MS. The fractionation was performed for 1 hour at ambient conditions.

Tables 1 and 2 show the mass of the five studied compounds PFNA, PFOS, PFOA, PFHxS, and PFBS at the beginning ("initial") and at the end ("froth", "depleted", and "water trap") of the foam fractionation as performed without aluminum ions (Table 1) and with aluminum ions (Table 2, +350 ppm Al). In Tables 1-2, "initial" refers to the initial mass of each of the compounds present in the volume of water to be fractionated, "froth" is the mass of compound collected in the froth (Body II), "depleted" is the mass of compound remaining in the bottom water after the process, "water trap" is the mass of compound in the water traps after the process, and "% removal" is the mass percentage of the PFAS compounds removed from the initial volume of water that was fractionated based on the mass of compounds in the depleted water ((initial-depleted)/initial). The results in Table 1A show that in the fractionation in the absence of aluminum, more than 90% of all compounds are removed from the water except for PFBS with a 42% removal. Table 1B gives the raw concentration data from the LC-MS used to generate the data in Table 1A. In the presence of 350 mg of aluminum in the initial volume of water to be fractionated, the results in Table 2A show a removal of greater than 90% in all cases, including for PFBS. Table 2B gives the raw concentration data from the LC-MS used to generate the data in Table 2A. In both experiments, the mass of compound collected in the water trap was very low, indicating a low volatilization value.

TABLE 1A

Initial, froth, depleted, water trap mass, and percentage removal of PFAS compounds without addition of aluminum.

| | PFNA (ng) | PFOS (ng) | PFOA (ng) | PFHxS (ng) | PFBS (ng) |
|---|---|---|---|---|---|
| Initial | 83 | 267 | 345 | 140 | 812 |
| Froth | 55.1 | 234.5 | 227.9 | 143.9 | 375.8 |
| Depleted | 7 | 7 | 10 | 7 | 471 |
| Water Trap | 0.3 | 0.7 | 2.8 | 0.3 | 0.3 |
| % Removal | 91.6 | 97.4 | 97.1 | 90.18 | 42.0 |

TABLE 1B

Initial, froth, depleted, and water trap concentrations, without addition of aluminum.

| | PFNA (ppt) | PFOS (ppt) | PFOA (ppt) | PFHxS (ppt) | PFBS (ppt) |
|---|---|---|---|---|---|
| Initial | 83 | 267 | 345 | 140 | 812 |
| Froth | 1377 | 5862 | 5697 | 3597 | 9394 |
| Depleted | 7 | 7 | 10 | 7 | 471 |
| Water Trap | 1 | 2 | 8 | 1 | 1 |

TABLE 2A

Initial, froth, depleted, water trap mass, and percentage removal of PFAS compounds with addition of 350 ppm aluminum.

| | PFNA (ng) | PFOS (ng) | PFOA (ng) | PFHxS (ng) | PFBS (ng) |
|---|---|---|---|---|---|
| Initial | 96 | 281 | 276 | 150 | 96 |
| Froth | 36 | 161.1 | 120.15 | 90.18 | 36 |
| Depleted | 7 | 7 | 7 | 7 | 7 |
| Water Trap | 0.06 | 0.35 | 0.175 | 0.035 | 0.06 |
| % Removal | 92.7 | 97.5 | 97.5 | 95.3 | 92.7 |

TABLE 2B

Initial, froth, depleted, and water trap concentrations, with addition of 350 ppm aluminum.

| | PFNA (ppt) | PFOS (ppt) | PFOA (ppt) | PFHxS (ppt) | PFBS (ppt) |
|---|---|---|---|---|---|
| Initial | 96 | 281 | 276 | 150 | 722 |
| Froth | 1200 | 5370 | 4005 | 3006 | 19818 |
| Depleted | 7 | 7 | 7 | 7 | 62 |
| Water Trap | 2 | 1 | 5 | 1 | 1 |

The foam was passed through a pipe and collected in a graduated cylinder. The volume of the initial, froth, depleted, and water trap portions was used to convert the concentration of these portions as measured by LC-MS to mass. Some foam was likely left on the walls at the top of the fractionator, in the pipe, and in the graduated cylinder, which is a possible explanation of why the water trap, depleted, and froth masses total to slightly less than the initial mass.

Example 2. Foam Separation of PFAS

Figure 7:
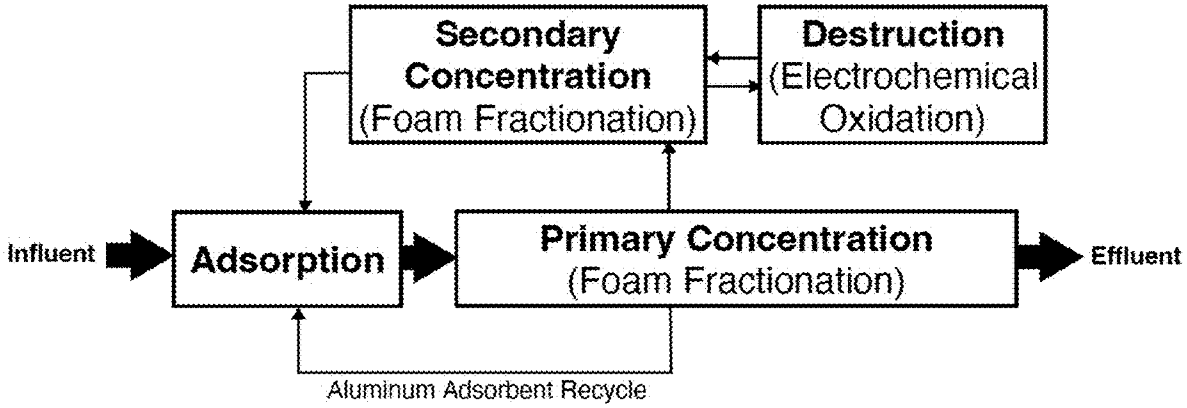
FIG. 7 illustrates a simplified process flow diagram of an apparatus used for foam separation of PFAS, in accordance with various aspects of the present invention.

A simplified process flow diagram of the apparatus used for foam separation of PFAS in this Example is shown in FIG. 7. A detailed process flow diagram of the apparatus is shown in FIG. 8. During the adsorption step, added aluminum concentrate (formed via dissolution of aluminum metal in HCl) formed aluminum hydroxide. The added aluminum concentrate had a pH of <2.7. The pH in the adsorption tank was between 4.5 and 5.2, and the adsorption tank had a concentration of aluminum of about 150 ppm. The conditions and retention times of the adsorption step were determined by treatability testing. During the primary concentration and effluent filtration step, sequential foam fractionation of the effluent water from the adsorption step was performed. During the primary concentration and effluent filtration step, the pH of the water was between 4.5 and 5.2. After sequential fractionator 3 and before the aluminum filtration, the water was basified to pH 6-7 via addition of sodium hydroxide. Filtration was used to recover solid aluminum hydroxide from the water. The recovered solid aluminum hydroxide, which included residual effluent water, was acidified to a pH of less than 4 prior to dissolve the majority of the aluminum hydroxide, which was then pumped back to the adsorption step. During the secondary concentration step, a hydrophobic foam fractionation was performed at low pH (greater than or equal to 2.6 to less than 4.0), separating PFAS and aluminum, and concentrating the PFAS for destructive treatment. The residual that remained after foaming in the secondary concentration step was recycled back to the adsorption step, thereby recycling both aluminum and the residual water. During the destruction step, the concentrated PFAS was treated with an electrolytic reactor to cause mineralization and destruction of the PFAS. The adsorption, primary concentration, and secondary concentration steps were performed continuously, while the destruction step was performed in a batch fashion. Concentrations of PFAS compounds were determined using LC-MS (via EPA method 1633 or 537). The TOC was determined via protocol SW846 using method 9060A. Aluminum concentration was measured via inductively coupled plasma (ICP). AOF was measured via combustion ion chromatography (CIC).

Figure 9:
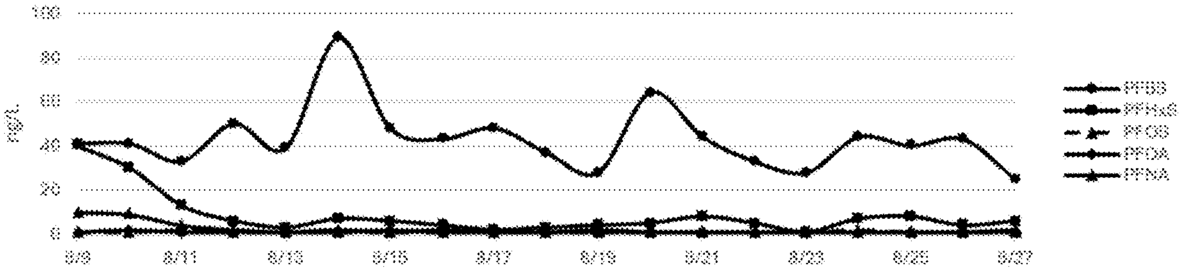
FIG. 9 illustrates a graph showing effluent concentrations of various PFAS after foam separation, in accordance with various aspects of the present invention.

A 26-day continuous flow test at 3 gph (72 gpd) was performed. The influent water was 1,760 gallons with >10,000 ng/L of total PFAS and >60 mg/L total organic carbon (TOC). The PFAS concentrations in the effluent water met maximum concentration limits (MCLs) for 19 consecutive days with a single pass through the system. The primary concentration generated 192 gallons which were further processed in the secondary concentration step. Table 3 illustrates the influent concentration, average effluent concentration, and average % removal for the measured components of the water. FIG. 9 illustrates a graph showing effluent concentrations of various PFAS during the 26-day continuous flow test at 3 gph.

TABLE 3

Influent concentration, average effluent concentration, and average % removal for the measured components.

| Analyte | Influent concentration | Average effluent concentration | Average % removal |
|---|---|---|---|
| PFBS (ng/L) | 61 | 43 | 29.4% |
| PFHxS (ng/L) | 594 | 9 | 98.6% |
| PFOS (ng/L) | 1,421 | 1 | 99.9% |
| PFOA (ng/L) | 318 | 1 | 99.7% |
| PFNA (ng/L) | 7,138 | 2 | 100.0% |
| TOC (mg/L) | 66 | 26 | 60.6% |
| DRO (mg/L) | 0.26 | 0.17 | 34.6% |
| GRO (mg/L) | 0.58 U | 0.1 | 82.8% |
| AOF (μg/L) | 9.1 J | 1.0 U | 89.0% |
| Aluminum (μg/L) | 49 | 94 | NA |

DRO = diesel range organics.
GRO = gasoline range organics.
AOF = adsorbable organic fluorine.
U = compound was analyzed for but not detected; method detection limit reported.
J = concentration is an approximate value.

A 21-day continuous flow test was conducted at 2 gph (48 gpd). The influent water was 1,500 gallons having >40,000 ng/L of total PFAS and ~25,000 ng/L PFOS. During week 1, the process equipment and conditions were optimized. Aluminum was successfully recycled into the adsorption tank during the 13 days of treatment post optimization. The PFAS were concentrated into <1.2 L (0.32 gallons), a >3,600× volume reduction, from the influent volume of 1,150 gallons with only the lead portion of the secondary concentration completed. An additional 20 to 50-times concentration yielding a total of 100,000× volume reduction could be expected but insufficient volume existed to complete the lag fractionation during this test. The volume reduction suggests that a 20-gpm system (10.5 M gal/yr) achieving 100,000× concentration factor could yield as little as 100 gallons for destruction annually. Table 4 illustrates PFAS concentration of influent and effluent water during the 21-day continuous flow test.

TABLE 4

PFAS concentration of influent and effluent water during the 21-day continuous flow test.

| | PFAS concentration (ng/L) | | Average % |
|---|---|---|---|
| Analyte | Influent | Treated effluent 13-day average | removal |
| PFBS | 245 | 153 | 37.60% |
| PFHxS | 15,133 | 9 | 99.90% |
| PFOS | 24,964 | 11 | 100.00% |
| PFOA | 1,267 | 1 | 99.90% |
| PFNA | 1,443 | 2 | 99.90% |

A 5-day continuous flow test was conducted at 2 gph (48 gpd). The influent water was 240 gallons having >680,000 ng/L total PFAS and ~480,000 ng/L PFOS. The operating conditions were consistent with those used for the 21-day run. The test resulted in >99.9% removal of all regulated compounds. The test demonstrated that he process is adaptable to influent water having inconsistent or higher PFAS concentrations. This non-optimized test demonstrated that operating costs are not impacted by higher PFAS concentration in influent water. Table 5 illustrates PFAS concentration of influent and effluent water during the 5-day continuous flow test.

TABLE 5

PFAS concentration of influent and effluent water during the 5-day continuous flow test.

| | PFAS concentration (ng/L) | | |
|---|---|---|---|
| Analyte | Influent | Treated effluent 5-day average | Average % removal |
| PFHxS | 160,000 | 161 | 99.90% |
| PFOS | 480,000 | 36 | 99.99% |
| PFOA | 6,300 | 1 | 99.98% |
| PFNA | 420 U | 1 | — |

U = compound was analyzed for but not detected; method detection limit reported.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Aspect 1 provides a method of concentrating a fluoroalkyl compound, the method comprising:

bubbling a gas into an aqueous solution comprising the fluoroalkyl compound and having a pH of 0 to 5.5 to form a foam comprising the fluoroalkyl compound; and removing the foam from the aqueous solution to form a concentrate comprising the fluoroalkyl compound and to form a clarified aqueous solution.

Aspect 2 provides the method of Aspect 1, wherein the fluoroalkyl compound is a perfluoroalkyl or polyfluoroalkyl substance (PFAS), perfluoroalkyl substance, a polyfluoroalkyl substance, a perfluoroalkyl acid (PFAA), or a combination thereof.

Aspect 3 provides the method of any one of Aspects 1-2, wherein the fluoroalkyl compound is perfluorooctanesulfonic acid (PFOA), perfluorooctyl sulfonate (PFOS), perfluorohexanesulfonic acid (PFHxS), perfluorononanoic acid (PFNA), perfluorobutanesulfonic acid (PFBS), 2-(N-methyl-perfluorooctane sulfonamido) acetic acid, perfluoroheptanoic acid (PFHpA), n-perfluorooctane sulfonic acid, perfluoromethylheptane sulfonic acid, n-perfluorooctanoic acid, a branched perfluorooctanoic acid, perfluorodecanoic acid, perfluoroundecanoic acid, perfluorododecanoic acid, hexafluoropropylene oxide-dimer acid (HFPO-DA), trifluoroacetic acid (TFA), trifluoromethanesulfonic acid (TFMS), or a combination thereof.

Aspect 4 provides the method of any one of Aspects 1-3, wherein the gas comprises air, nitrogen, oxygen, ozone, argon, hydrogen, helium, or a combination thereof.

Aspect 5 provides the method of any one of Aspects 1-4, wherein the bubbling of the gas into the aqueous solution forms nanobubbles, microbubbles, or a combination thereof.

Aspect 6 provides the method of any one of Aspects 1-5, wherein the bubbling of the gas into the aqueous solution forms bubbles having a diameter of 1 nm to 10 mm.

Aspect 7 provides the method of any one of Aspects 1-6, wherein the bubbling comprises flowing the gas into an aeration apparatus that is submerged in the aqueous solution.

Aspect 8 provides the method of Aspect 7, wherein the aeration apparatus comprises a gas sparger, a perforated pipe, a sparging rod, a serrated cone, a diffuser ring, a stone diffuser, or a combination thereof.

Aspect 9 provides the method of any one of Aspects 7-8, wherein the aeration apparatus comprises a stone diffuser.

Aspect 10 provides the method of any one of Aspects 1-9, wherein the aqueous solution comprises water from a natural source, an extract from contaminated soil, an extract from contaminated landfill materials, water contaminated with residual fire-fighting foam, industrial waste water, a concentrate of any one or any combination thereof, or a combination thereof.

Aspect 11 provides the method of any one of Aspects 1-10, wherein the aqueous solution has a pH of 0 to 5.2.

Aspect 12 provides the method of any one of Aspects 1-11, wherein the aqueous solution has a pH of 4.5 to 5.2.

Aspect 13 provides the method of any one of Aspects 1-12, further comprising adding one or more acids and/or bases to the aqueous solution before or during the bubbling to achieve and/or maintain the pH of 0 to 5.5.

Aspect 14 provides the method of Aspect 13, wherein the one or more acids comprise HCl, HBr, $HNO_3$, $H_2SO_4$, $HClO_4$, $HClO_3$, or a combination thereof.

Aspect 15 provides the method of any one of Aspects 13-14, wherein the one or more acids comprise HCl, $H_2SO_4$, or a combination thereof.

Aspect 16 provides the method of any one of Aspects 1-15, wherein the aqueous solution has a concentration of the fluoroalkyl compound of 0.001 ppt to 100,000 ppm.

Aspect 17 provides the method of any one of Aspects 1-16, wherein the aqueous solution has a concentration of the fluoroalkyl compound of 0.001 ppt to 100 ppm.

Aspect 18 provides the method of any one of Aspects 1-17, wherein the removing of the foam from the aqueous solution comprises scooping the foam from a surface of the aqueous concentrate, vacuuming the foam from a surface of the aqueous concentrate, pushing the foam off a surface of the aqueous concentrate, or a combination thereof.

Aspect 19 provides the method of any one of Aspects 1-18, wherein the method further comprises breaking the foam, to form the concentrate.

Aspect 20 provides the method of any one of Aspects 1-19, wherein the concentrate has a concentration of the fluoroalkyl compound of 0.005 ppt to 500,000 ppm, as measured with the concentrate substantially free of bubbles and foam.

Aspect 21 provides the method of any one of Aspects 1-20, wherein the concentrate has a concentration of the fluoroalkyl compound of 0.005 ppt to 1,000 ppm.

Aspect 22 provides the method of any one of Aspects 1-21, wherein a ratio of a concentration of the fluoroalkyl compound in the aqueous solution to a concentration of the fluoroalkyl compound in the concentrate is 1:2 to 1:2,000,000.

Aspect 23 provides the method of any one of Aspects 1-22, wherein a ratio of a concentration of the fluoroalkyl compound in the aqueous solution to a concentration of the fluoroalkyl compound in the concentrate is 1:5 to 1:40.

Aspect 24 provides the method of any one of Aspects 1-23, wherein the clarified aqueous solution has a concentration of the fluoroalkyl compound of 0.0001 ppt to 100 ppm.

Aspect 25 provides the method of any one of Aspects 1-24, wherein the clarified aqueous solution has a concentration of the fluoroalkyl compound of 0.0001 ppt to 10 ppt.

Aspect 26 provides the method of any one of Aspects 1-25, wherein the clarified aqueous solution has a concentration of the fluoroalkyl compound of 0.0001 ppt to 4 ppt.

Aspect 27 provides the method of any one of Aspects 1-26, wherein a ratio of a concentration of the fluoroalkyl compound in the clarified aqueous solution to a concentration of the fluoroalkyl compound in the aqueous solution is 1:2 to 1:1000.

Aspect 28 provides the method of any one of Aspects 1-27, wherein a ratio of a concentration of the fluoroalkyl compound in the clarified aqueous solution to a concentration of the fluoroalkyl compound in the aqueous solution is 1:5 to 1:40.

Aspect 29 provides the method of any one of Aspects 1-28, wherein the aqueous solution having had the foam removed therefrom is a second aqueous solution, further comprising bubbling the gas into the second aqueous solution to form a second foam and removing the second foam from the second aqueous solution, and combining the foam removed from the aqueous solution and the second foam to form the concentrate comprising the fluoroalkyl compound, and wherein the second aqueous solution having the second foam removed therefrom is the clarified aqueous solution.

Aspect 30 provides the method of Aspect 29, wherein the second aqueous solution having had the second foam removed therefrom is a third aqueous solution, further comprising bubbling the gas into the third aqueous solution to form a third foam and removing the third foam from the third aqueous solution, and combining the foam removed from the aqueous solution, the second foam, and the third foam to form the concentrate comprising the fluoroalkyl compound and wherein the third aqueous solution having the foam removed therefrom is the clarified aqueous solution.

Aspect 31 provides the method of Aspect 30, further comprising repeating sequential foaming of the aqueous solution more than two times, and combining the removed foams to form the concentrate comprising the fluoroalkyl compound, and wherein the sequentially foamed aqueous solution having the foams removed therefrom is the clarified aqueous solution.

Aspect 32 provides the method of any one of Aspects 1-31, further comprising performing the bubbling of the gas into the aqueous solution comprising the fluoroalkyl compound and having a pH of 0 to 5.5 to form the form comprising the fluoroalkyl compound and the removing of the foam from the aqueous solution to form the concentrate comprising the fluoroalkyl compound and to form a clarified aqueous solution two or more times using the concentrate as the aqueous solution in each iteration of the two or more times.

Aspect 33 provides the method of Aspect 32, further comprising recycling the clarified aqueous solution formed from the second or higher iteration of the two or more times back to the aqueous solution used in the first foaming step of the method.

Aspect 34 provides the method of Aspect 32-33, wherein during a second or higher iteration of the two or more times, a pH range of the aqueous solution is 0 to less than 4.

Aspect 35 provides the method of any one of Aspects 32-34, wherein during a second or higher iteration of the two or more times, a pH range of the aqueous solution is 2.5 to less than 4.

Aspect 36 provides the method of any one of Aspects 32-35, wherein during a second or higher iteration of the two or more times, the aqueous solution having had the foam removed therefrom is a second aqueous solution, further comprising bubbling the gas into the second aqueous solution to form a second foam and removing the second foam from the second aqueous solution, and combining the foam removed from the aqueous solution and the second foam to form the concentrate comprising the fluoroalkyl compound, and wherein the second aqueous solution having the second foam removed therefrom is the clarified aqueous solution.

Aspect 37 provides the method of Aspect 36, wherein during the second or higher iteration of the two or more times, the second aqueous solution having had the second foam removed therefrom is a third aqueous solution, further comprising bubbling the gas into the third aqueous solution to form a third foam and removing the third foam from the third aqueous solution, and combining the foam removed from the aqueous solution, the second foam, and the third foam to form the concentrate comprising the fluoroalkyl compound and wherein the third aqueous solution having the foam removed therefrom is the clarified aqueous solution.

Aspect 38 provides the method of Aspect 37, during the second or higher iteration of the two or more times, further comprising repeating sequential foaming of the aqueous solution more than two times, and combining the removed foams to form the concentrate comprising the fluoroalkyl compound, and wherein the sequentially foamed aqueous solution having the foams removed therefrom is the clarified aqueous solution.

Aspect 39 provides the method of any one of Aspects 32-38, further comprising recycling the clarified aqueous solution formed from the second or higher iteration of the two or more times back to the aqueous solution used in the first foaming step of the method.

Aspect 40 provides the method of any one of Aspects 32-39, comprising performing the bubbling of the gas into the aqueous solution comprising the fluoroalkyl compound to form the foam comprising the fluoroalkyl compound and the removing of the foam from the aqueous solution to form the concentrate comprising the fluoroalkyl compound and to form the clarified aqueous solution one or more additional times using the concentrate formed by combining the foam and any additional foams as the aqueous solution in each of the one or more additional times.

Aspect 41 provides the method of any one of Aspects 32-40, comprising recycling the clarified aqueous solution formed from performing the bubbling of the gas into the aqueous solution comprising the fluoroalkyl compound to form the foam comprising the fluoroalkyl compound and the removing of the foam from the aqueous solution to form the concentrate comprising the fluoroalkyl compound and to form the clarified aqueous solution the one or more additional times back to the aqueous solution used in the first foaming step of the method.

Aspect 42 provides the method of Aspect 32, wherein a ratio of a concentration of the fluoroalkyl compound in the aqueous solution used in the first iteration of the two or more times to a concentration of the fluoroalkyl compound in the concentrate formed by the last iteration of the two or more times is 1:4 to 1:100,000.

Aspect 43 provides the method of any one of Aspects 32-42, wherein a ratio of a concentration of the fluoroalkyl compound in the aqueous solution used in the first iteration of the two or more times to a concentration of the fluoroalkyl compound in the concentrate formed by the last iteration of the two or more times is 1:10 to 1:80.

Aspect 44 provides the method of any one of Aspects 1-28, wherein the aqueous solution having had the foam removed therefrom is a second aqueous solution, further comprising bubbling the gas into the second aqueous solution to form a second foam and removing the second foam from the second aqueous solution, and combining the foam removed from the aqueous solution and the second foam to form the concentrate comprising the fluoroalkyl compound, and wherein the second aqueous solution having the second foam removed therefrom is the clarified aqueous solution;

performing the bubbling of the gas into the aqueous solution comprising the fluoroalkyl compound to form the form comprising the fluoroalkyl compound and the removing of the foam from the aqueous solution to form the concentrate comprising the fluoroalkyl compound and to form a clarified aqueous solution two or more times using the concentrate as the aqueous solution in each iteration of the two or more times, wherein during a second or higher iteration of the two or more times a pH range of the aqueous solution is 0 to less than 4;

wherein during a second or higher iteration of the two or more times, the aqueous solution having had the foam removed therefrom is a secondary second aqueous solution, further comprising bubbling the gas into the secondary second aqueous solution to form a secondary second foam and removing the secondary second foam from the secondary second aqueous solution, and combining the foam removed from the aqueous solution in the first iteration of the two or more times and the secondary second foam to form the concentrate comprising the fluoroalkyl compound, and wherein the secondary second aqueous solution having the secondary second foam removed therefrom is a secondary clarified aqueous solution; and recycling the secondary clarified aqueous solution formed from the second or higher iteration of the two or more times back to the aqueous solution used in the first foaming step of the method.

Aspect 45 provides the method of any one of Aspects 1-44, further comprising destroying the fluoroalkyl compound.

Aspect 46 provides the method of Aspect 45, comprising destroying the fluoroalkyl compound during the bubbling.

Aspect 47 provides the method of any one of Aspects 45-46, comprising destroying the fluoroalkyl compound in the concentrate.

Aspect 48 provides the method of any one of Aspects 45-47, wherein the destroying comprises thermal treatment, treatment with an electrolytic cell, plasma reactor, supercritical water, combustion, oxidation, chemical treatment, or a combination thereof.

Aspect 49 provides the method of any one of Aspects 45-48, wherein the destroying comprises treatment with an electrolytic cell.

Aspect 50 provides the method of any one of Aspects 1-49, further comprising concentrating the fluoroalkyl compound from a feed water comprising the fluoroalkyl compound, to form the aqueous solution.

Aspect 51 provides the method of Aspect 50, wherein the feed water comprises water from a natural source, an extract from contaminated soil, an extract from contaminated landfill materials, water contaminated with residual fire-fighting foam, industrial waste water, a concentrate of any one or any combination thereof, or a combination thereof.

Aspect 52 provides the method of any one of Aspects 50-51, wherein the feed water has a concentration of the fluoroalkyl compound of 0.001 ppt to 100,000 ppm.

Aspect 53 provides the method of any one of Aspects 50-52, wherein the feed water has a concentration of the fluoroalkyl compound of 0.001 ppt to 100 ppm.

Aspect 54 provides the method of any one of Aspects 50-53, wherein a ratio of a concentration of the fluoroalkyl compound in the feed water to a concentration of the fluoroalkyl compound in the aqueous solution is 1:2 to 1:2,000,000.

Aspect 55 provides the method of any one of Aspects 50-54, wherein a ratio of a concentration of the fluoroalkyl compound in the feed water to a concentration of the fluoroalkyl compound in the aqueous solution is 1:2 to 1:50.

Aspect 56 provides the method of any one of Aspects 50-55, wherein the concentrating the fluoroalkyl compound from the feed water comprises treatment of the feed water with a sorbent, treatment of the feed water with a metal component, treatment of the feed water with a galvanic or electrolytic cell, clarification of the feed water, filtration of the feed water (e.g., membrane filtration), flotation separation of the feed water, or a combination thereof.

Aspect 57 provides the method of any one of Aspects 50-56, wherein the concentrating the fluoroalkyl compound from the feed water comprises contacting the feed water with a galvanic cell to form solids in the feed water that comprise a metal from an electrode of the galvanic cell;

removing the solids from the feed water, to form a clarified feed water and to form a feed water concentrate comprising the removed solids; and acidifying the feed water comprising the removed solids to form the aqueous solution.

Aspect 58 provides the method of Aspect 57, wherein the galvanic cell comprises an anode comprising aluminum and a cathode comprising copper.

Aspect 59 provides the method of Aspect 58, wherein the galvanic cell further comprises a conductive connector that physically and electrically connects the anode and cathode to one another.

Aspect 60 provides the method of Aspect 59, wherein the conductive connector maintains a gap between the anode and the cathode.

Aspect 61 provides the method of any one of Aspects 50-60, wherein the concentrating the fluoroalkyl compound from the feed water comprises treating the feed water with a metal component comprising a metal;

removing solids comprising the metal component from the feed water, to form a clarified feed water and to form a feed water concentrate comprising the removed solids; and acidifying the feed water concentrate comprising the removed solids to form the aqueous solution.

Aspect 62 provides the method of Aspect 61, wherein the metal of the metal component comprises Mg, Al, Fe, Zn, Cu, Cd, Cr, Hg, Ni, V, Ce, or a combination thereof.

Aspect 63 provides the method of any one of Aspects 61-62, wherein the metal of the metal component comprises Al.

Aspect 64 provides the method of any one of Aspects 57-63, wherein the acidifying comprises adding HCl, HBr, $HNO_3$, $H_2SO_4$, $HClO_4$, $HClO_3$, or a combination thereof.

Aspect 65 provides the method of any one of Aspects 57-64, wherein the clarified aqueous solution comprises the metal from the electrode or the metal component, wherein the method further comprises recycling the metal from the electrode or the metal component, the recycling comprising reusing the metal from the electrode or the metal component in the aqueous solution in a subsequent iteration of the method.

Aspect 66 provides the method of Aspect 65, further comprising purging one or more contaminants from a recycle stream, wherein the recycle stream comprises the metal from the electrode or the metal component that is reused in the aqueous solution in the subsequent iteration of the method.

Aspect 67 provides the method of any one of Aspects 1-66, wherein the method further comprises adding an additive to the aqueous solution, or adding an additive to a feed water from which the fluoroalkyl compound in the aqueous solution is concentrated.

Aspect 68 provides the method of Aspect 67, wherein the adding the additive to the aqueous solution comprises generating the additive in the aqueous solution using a galvanic cell.

Aspect 69 provides the method of any one of Aspects 67-68, wherein the additive comprises $AlCl_3$, $Al(OH)_3$, $AlPO_4$, $Al_2(SO_4)_3$, or a combination thereof.

Aspect 70 provides the method of any one of Aspects 67-69, wherein the additive comprises a metal component comprising a metal.

Aspect 71 provides the method of Aspect 70, wherein the metal of the metal component comprises Mg, Al, Fe, Zn, Cu, Cd, Cr, Hg, Ni, V, Ce, or a combination thereof.

Aspect 72 provides the method of any one of Aspects 70-71, wherein the metal of the metal component comprises Al.

Aspect 73 provides the method of any one of Aspects 67-72, wherein the clarified aqueous solution comprises the additive.

Aspect 74 provides the method of Aspect 73, further comprising reusing the additive in the clarified aqueous solution and/or a metal from the additive in the clarified aqueous solution in the additive in a subsequent iteration of the method.

Aspect 75 provides the method of Aspect 74, wherein the reusing of the additive and/or the metal therefrom comprises flowing a recycle stream comprising at least part of the clarified aqueous solution or an extract thereof to the aqueous solution of the subsequent iteration of the method or to a feed water from which the fluoroalkyl compound in the aqueous solution is concentrated of the subsequent iteration of the method.

Aspect 76 provides the method of any one of Aspects 74-75, wherein the reusing of the additive and/or the metal therefrom further comprises purging one or more acidification contaminants from the additive and/or the metal therefrom prior to the reuse of the additive and/or metal therefrom in the subsequent iteration of the method.

Aspect 77 provides the method of Aspect 76, wherein the purging comprises purging the one or more acidification contaminants from a recycle stream comprising at least part of the clarified aqueous solution or an extract thereof prior to the reuse of the additive and/or metal therefrom in the subsequent iteration of the method.

Aspect 78 provides the method of any one of Aspects 76-77, wherein the purging comprises separating sulfate, chloride, or a combination thereof, from the additive and/or metal therefrom.

Aspect 79 provides the method of any one of Aspects 76-78, comprising adding a base to a recycle stream comprising at least part of the clarified aqueous solution or an extract thereof to raise a pH thereof to 3 to 6, filtering out a precipitated salt comprising the one or more acidification contaminants from the recycle stream, and adding the filtered recycle stream to the aqueous solution or a feed water from which the fluoroalkyl compound in the aqueous solution is concentrated.

Aspect 80 provides the method of any one of Aspects 76-79, comprising adding a base to a recycle stream comprising at least part of the clarified aqueous solution or an extract thereof to raise a pH thereof to 3 to 6, and filtering out a precipitated salt comprising the additive from the recycle stream, and adding the precipitated salt to the aqueous solution or a feed water from which the fluoroalkyl compound in the aqueous solution is concentrated.

Aspect 81 provides a method of concentrating a fluoroalkyl compound, the method comprising:

bubbling a gas into an aqueous solution comprising the fluoroalkyl compound, an additive, and having a pH of 0 to 5.5 to form a foam comprising the fluoroalkyl compound, wherein the additive comprises a metal component comprising a metal; and removing the foam from the aqueous solution to form a concentrate comprising the fluoroalkyl compound and to form a clarified aqueous solution.

Aspect 82 provides the method of Aspect 81, wherein the metal comprises aluminum.

Aspect 83 provides the method of any one of Aspects 81-82, wherein the metal component comprises $AlCl_3$, $Al(OH)_3$, $AlPO_4$, $Al_2(SO_4)_3$, or a combination thereof.

Aspect 84 provides the method of any one of Aspects 81-83, wherein the aqueous solution has a concentration of the metal component of 0.01 ppm to 800 ppm.

Aspect 85 provides the method of any one of Aspects 81-84, wherein the fluoroalkyl compound is perfluorooctanesulfonic acid (PFOA), perfluorooctyl sulfonate (PFOS), perfluorohexanesulfonic acid (PFHxS), perfluorononanoic acid (PFNA), perfluorobutanesulfonic acid (PFBS), 2-(N-methyl-perfluorooctane sulfonamido) acetic acid, perfluoroheptanoic acid (PFHpA), n-perfluorooctane sulfonic acid, perfluoromethylheptane sulfonic acid, n-perfluorooctanoic acid, a branched perfluorooctanoic acid, perfluorodecanoic acid, perfluoroundecanoic acid, perfluorododecanoic acid, hexafluoropropylene oxide-dimer acid (HFPO-DA), trifluoroacetic acid (TFA), trifluoromethanesulfonic acid (TFMS), or a combination thereof.

Aspect 86 provides the method of any one of Aspects 81-85, wherein the gas comprises air, nitrogen, oxygen, ozone, argon, hydrogen, helium, or a combination thereof.

Aspect 87 provides the method of any one of Aspects 81-86, wherein the aqueous solution has a pH of 4.5 to 5.2.

Aspect 88 provides the method of any one of Aspects 81-87, wherein the aqueous solution has a concentration of the fluoroalkyl compound of 0.1 parts-per-trillion (ppt) to 100,000 parts-per-million (ppm).

Aspect 89 provides the method of any one of Aspects 81-88, wherein a ratio of a concentration of the fluoroalkyl compound in the aqueous solution to a concentration of the fluoroalkyl compound in the concentrate is 1:2 to 1:2,000,000, as measured with the concentrate substantially free of bubbles and foam.

Aspect 90 provides the method of any one of Aspects 81-89, further comprising destroying the fluoroalkyl compound.

Aspect 91 provides the method of any one of Aspects 81-90, wherein the aqueous solution having the foam removed therefrom is a second aqueous solution, further comprising a second bottoms iteration comprising:

bubbling the gas into the second aqueous solution having the foam removed therefrom to form a second foam comprising the fluoroalkyl compound; and removing the second foam from second aqueous solution to form a second concentrate comprising the fluoroalkyl compound and to form a second clarified aqueous solution;

combining the foam and the second foam to form the concentrate.

Aspect 92 provides the method of any one of Aspects 81-91, further comprising a second iteration of the bubbling and foam removal comprising:

bubbling the gas into the concentrate to form a secondary foam comprising the fluoroalkyl compound; and removing the secondary foam from the concentrate to form a secondary concentrate comprising the fluoroalkyl compound and a secondary clarified aqueous solution.

Aspect 93 provides the method of Aspect 92, wherein during the second or a higher iteration of the bubbling and foam removal, the concentrate has a pH of 0 to less than 4.

Aspect 94 provides the method of any one of Aspects 92-93, further comprising recycling the secondary clarified aqueous solution back to the aqueous solution used in a first bubbling and foam removal step of the method.

Aspect 95 provides the method of any one of Aspects 92-94, further comprising a second tops iteration comprising:

bubbling the gas into the secondary clarified aqueous solution to form a tertiary foam comprising the fluoroalkyl compound;

removing the tertiary foam from the concentrate to form a tertiary concentrate comprising the fluoroalkyl compound and a tertiary clarified aqueous solution; and combining the secondary concentrate and the tertiary concentrate to form a combined concentrate.

Aspect 96 provides the method of any one of Aspects 92-95, further comprising a third iteration of the bubbling and foam removal comprising:

bubbling the gas into the secondary concentrate to form a third foam comprising the fluoroalkyl compound; and removing the third foam from the secondary concentrate to form a third concentrate comprising the fluoroalkyl compound and a third clarified aqueous solution.

Aspect 97 provides the method of Aspect 96, further comprising recycling the third clarified aqueous solution back to the aqueous solution used in a first bubbling and foam removal step of the method.

Aspect 98 provides the method of any one of Aspects 81-97, wherein the clarified aqueous solution comprises the metal, further comprising reusing the metal in the clarified aqueous solution in the aqueous solution in a subsequent iteration of the method, wherein the reusing of the metal comprises flowing a recycle stream comprising at least part of the clarified aqueous solution or an extract thereof to the aqueous solution of the subsequent iteration of the method.

Aspect 99 provides a method of concentrating a fluoroalkyl compound, the method comprising:

bubbling a gas into an aqueous solution to form a foam comprising the fluoroalkyl compound, wherein the aqueous solution has a pH of 0 to 5.5 and comprises the fluoroalkyl compound at a concentration of 0.1 ppt to 100,000 ppm, an additive comprising a metal component that comprises a metal;

removing the foam from the aqueous solution to form a concentrate comprising the fluoroalkyl compound and to form a clarified aqueous solution comprising the metal of the metal component of the additive, wherein a ratio of a concentration of the fluoroalkyl compound in the aqueous solution to a concentration of the fluoroalkyl compound in the concentrate is 1:2 to 1:2,000,000; and reusing the metal from the clarified aqueous solution or an extract thereof, the reusing comprising adding the metal to the aqueous solution of a subsequent iteration of the method or to feed water from which the fluoroalkyl compound in the aqueous solution is concentrated in the subsequent iteration of the method.

Aspect 100 provides a method of concentrating a fluoroalkyl compound, the method comprising:

bubbling a gas into an aqueous solution comprising the fluoroalkyl compound at a concentration of 0.1 ppt to 100,000 ppm and an additive comprising a metal component that comprises aluminum to form a foam comprising the fluoroalkyl compound, wherein the aqueous solution has a pH of 0 to 5.5;

removing the foam from the aqueous solution, wherein the aqueous solution having had the foam removed therefrom is a second aqueous solution;

bubbling the gas into the second aqueous solution to form a second foam and removing the second foam from the second aqueous solution, and combining the foam removed from the aqueous solution and the second foam to form a concentrate comprising the fluoroalkyl compound, and wherein the second aqueous solution having the second foam removed therefrom is a clarified aqueous solution comprising the aluminum of the metal component;

reusing the aluminum in the clarified aqueous solution or an extract thereof, the reusing comprising adding the aluminum to the aqueous solution;

bubbling the gas into the concentrate to form a secondary foam comprising the fluoroalkyl compound the removing the secondary foam from the concentrate to form a secondary concentrate comprising the fluoroalkyl compound and to form a secondary clarified aqueous solution, wherein during the formation of the secondary foam the concentrate has a pH of 0 to less than 4, wherein a ratio of a concentration of the fluoroalkyl compound in the aqueous solution to a concentration of the fluoroalkyl compound in the secondary concentrate is 1:2 to 1:2,000,000; and recycling the secondary clarified aqueous solution back to the aqueous solution.

Aspect 101 provides the method of any one or any combination of Aspects 1-100 optionally configured such that all elements or options recited are available to use or select from.

What is claimed is:

1. A method of concentrating a fluoroalkyl compound, the method comprising:

bubbling a gas into an aqueous solution comprising the fluoroalkyl compound, an additive, and having a pH of 0 to 5.5 to form a foam comprising the fluoroalkyl compound, wherein the additive comprises a metal component comprising a metal;

removing the foam from the aqueous solution to form a concentrate comprising the fluoroalkyl compound and to form a clarified aqueous solution wherein the clarified aqueous solution comprises the metal; and reusing the metal in the clarified aqueous solution or an extract thereof in the aqueous solution in a subsequent iteration of the method, wherein the reusing of the metal comprises basifying the clarified aqueous solution or the extract thereof to a pH of 5.5 to 7.5 to precipitate the metal component, separating the precipitated metal component from the clarified aqueous solution or the extract thereof;

acidifying the separated metal component to a pH of 0 to 4.5, and flowing a recycle stream comprising the acidified metal component to the aqueous solution of the subsequent iteration of the method.

2. The method of claim 1, wherein the metal comprises aluminum.

3. The method of claim 1, wherein the metal component comprises $AlCl_3$, $Al(OH)_3$, $AlPO_4$, $Al_2(SO_4)_3$, or a combination thereof.

4. The method of claim 1, wherein the aqueous solution has a concentration of the metal component of 0.01 parts-per-million (ppm) to 800 ppm.

5. The method of claim 1, wherein the fluoroalkyl compound is perfluorooctanesulfonic acid (PFOA), perfluorooctyl sulfonate (PFOS), perfluorohexanesulfonic acid (PFHxS), perfluorononanoic acid (PFNA), perfluorobutanesulfonic acid (PFBS), 2-(N-methyl-perfluorooctane sulfonamido) acetic acid, perfluoroheptanoic acid (PFHpA), n-perfluorooctane sulfonic acid, perfluoromethylheptane sulfonic acid, n-perfluorooctanoic acid, a branched perfluorooctanoic acid, perfluorodecanoic acid, perfluoroundecanoic acid, perfluorododecanoic acid, hexafluoropropylene oxide-dimer acid (HFPO-DA), trifluoroacetic acid (TFA), trifluoromethanesulfonic acid (TFMS), or a combination thereof.

6. The method of claim 1, wherein the gas comprises air, nitrogen, oxygen, ozone, argon, hydrogen, helium, or a combination thereof.

7. The method of claim 1, wherein the aqueous solution has a pH of 4.5 to 5.2.

8. The method of claim 1, wherein the aqueous solution has a concentration of the fluoroalkyl compound of 0.1 parts-per-trillion (ppt) to 100,000 parts-per-million (ppm).

9. The method of claim 1, wherein a ratio of a concentration of the fluoroalkyl compound in the aqueous solution to a concentration of the fluoroalkyl compound in the concentrate is 1:2 to 1:2,000,000, as measured with the concentrate substantially free of bubbles and foam.

10. The method of claim 1, further comprising destroying the fluoroalkyl compound.

11. The method of claim 1, wherein the aqueous solution having the foam removed therefrom is a second aqueous solution, further comprising a second bottoms iteration comprising:

bubbling the gas into the second aqueous solution having the foam removed therefrom to form a second foam comprising the fluoroalkyl compound; and removing the second foam from second aqueous solution to form a second concentrate comprising the fluoroalkyl compound and to form a second clarified aqueous solution;

combining the foam and the second foam to form the concentrate.

12. The method of claim 1, further comprising a second iteration of the bubbling and foam removal comprising:

bubbling the gas into the concentrate to form a secondary foam comprising the fluoroalkyl compound; and removing the secondary foam from the concentrate to form a secondary concentrate comprising the fluoroalkyl compound and a secondary clarified aqueous solution.

13. The method of claim 12, wherein during the second or a higher iteration of the bubbling and foam removal, the concentrate has a pH of 0 to less than 4.

14. The method of claim 12, further comprising recycling the secondary clarified aqueous solution back to the aqueous solution used in a first bubbling and foam removal step of the method.

15. The method of claim 12, further comprising a second tops iteration comprising:

bubbling the gas into the secondary clarified aqueous solution to form a tertiary foam comprising the fluoroalkyl compound;

removing the tertiary foam from the concentrate to form a tertiary concentrate comprising the fluoroalkyl compound and a tertiary clarified aqueous solution; and combining the secondary concentrate and the tertiary concentrate to form a combined concentrate.

16. The method of claim 12, further comprising a third iteration of the bubbling and foam removal comprising:

bubbling the gas into the secondary concentrate to form a third foam comprising the fluoroalkyl compound; and removing the third foam from the secondary concentrate to form a third concentrate comprising the fluoroalkyl compound and a third clarified aqueous solution.

17. The method of claim 16, further comprising recycling the third clarified aqueous solution back to the aqueous solution used in a first bubbling and foam removal step of the method.

18. A method of concentrating a fluoroalkyl compound, the method comprising:

bubbling a gas into an aqueous solution to form a foam comprising the fluoroalkyl compound, wherein the aqueous solution has a pH of 0 to 5.5 and comprises the fluoroalkyl compound at a concentration of 0.1 ppt to 100,000 ppm, an additive comprising a metal component that comprises a metal that comprises aluminum;

removing the foam from the aqueous solution to form a concentrate comprising the fluoroalkyl compound and to form a clarified aqueous solution comprising the metal of the metal component of the additive, wherein a ratio of a concentration of the fluoroalkyl compound in the aqueous solution to a concentration of the fluoroalkyl compound in the concentrate is 1:2 to 1:2,000,000; and reusing the metal from the clarified aqueous solution or an extract thereof, the reusing comprising basifying the clarified aqueous solution or the extract thereof to a pH of 5.5 to 7.5 to precipitate the metal component, separating the precipitated metal component from the clarified aqueous solution or the extract thereof, acidifying the separated metal component to a pH of 0 to 4.5, and flowing a recycle stream comprising the acidified metal component to the aqueous solution of a subsequent iteration of the method or to feed water from which the fluoroalkyl compound in the aqueous solution is concentrated in the subsequent iteration of the method.

19. A method of concentrating a fluoroalkyl compound, the method comprising:

bubbling a gas into an aqueous solution comprising the fluoroalkyl compound at a concentration of 0.1 ppt to 100,000 ppm and an additive comprising a metal component that comprises aluminum to form a foam comprising the fluoroalkyl compound, wherein the aqueous solution has a pH of 0 to 5.5;

removing the foam from the aqueous solution, wherein the aqueous solution having had the foam removed therefrom is a second aqueous solution;

bubbling the gas into the second aqueous solution to form a second foam and removing the second foam from the second aqueous solution, and combining the foam removed from the aqueous solution and the second foam to form a concentrate comprising the fluoroalkyl compound, and wherein the second aqueous solution having the second foam removed therefrom is a clarified aqueous solution comprising the aluminum of the metal component;

reusing the aluminum in the clarified aqueous solution or an extract thereof, the reusing comprising basifying the clarified aqueous solution or the extract thereof to a pH of 5.5 to 7.5 to precipitate the metal component, separating the precipitated metal component from the clarified aqueous solution of the extract thereof, acidifying the separated metal component to a pH of 0 to 4.5, and flowing a recycle stream comprising the acidified metal component to the aqueous solution;

bubbling the gas into the concentrate to form a secondary foam comprising the fluoroalkyl compound the removing the secondary foam from the concentrate to form a secondary concentrate comprising the fluoroalkyl compound and to form a secondary clarified aqueous solution, wherein during the formation of the secondary foam the concentrate has a pH of 0 to less than 4, wherein a ratio of a concentration of the fluoroalkyl compound in the aqueous solution to a concentration of the fluoroalkyl compound in the secondary concentrate is 1:2 to 1:2,000,000; and recycling the secondary clarified aqueous solution back to the aqueous solution.

* * * * *